(12) United States Patent
Baruch et al.

(10) Patent No.: US 11,452,819 B2
(45) Date of Patent: Sep. 27, 2022

(54) MEDICATION DELIVERY DEVICE WITH SENSING SYSTEM

(71) Applicant: Eli Lilly and Company, Indianapolis, IN (US)

(72) Inventors: Uri Eliezer Baruch, Saffron Walden (GB); James Angus Boonzaier, Cambridge (GB); Xorge Castro Pelayo, London (GB); Matthew James Clemente, Carmel, IN (US); Jeremy Peter Clements, Willingham (GB); James Alexander Davies, Upper Cambourne (GB); Robert Eugene Trzybinski, Westfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 687 days.

(21) Appl. No.: 16/467,314

(22) PCT Filed: Dec. 8, 2017

(86) PCT No.: PCT/US2017/065247
§ 371 (c)(1),
(2) Date: Jun. 6, 2019

(87) PCT Pub. No.: WO2018/111708
PCT Pub. Date: Jun. 21, 2018

(65) Prior Publication Data
US 2020/0078525 A1 Mar. 12, 2020

Related U.S. Application Data

(60) Provisional application No. 62/434,684, filed on Dec. 15, 2016.

(51) Int. Cl.
*A61M 5/315* (2006.01)
*A61M 5/24* (2006.01)
*A61M 5/31* (2006.01)

(52) U.S. Cl.
CPC ...... *A61M 5/31568* (2013.01); *A61M 5/2422* (2013.01); *A61M 5/31525* (2013.01);
(Continued)

(58) Field of Classification Search
None
See application file for complete search history.

(56) References Cited

U.S. PATENT DOCUMENTS

| 685,091 A | 10/1901 | Becton |
|---|---|---|
| 1,625,035 A | 4/1927 | Lilly |

(Continued)

FOREIGN PATENT DOCUMENTS

| EP | 0338806 | 10/1989 |
|---|---|---|
| EP | 0498737 | 8/1992 |

(Continued)

OTHER PUBLICATIONS

Eli Lilly and Company, Technical Dossier for the HumaPen® Pen-Injector Family, Aug. 15, 2000, pp. 1 and 10-25 provided.
(Continued)

*Primary Examiner* — Manuel A Mendez
(74) *Attorney, Agent, or Firm* — Arthur C. H. Shum

(57) ABSTRACT

A medication delivery device with a sensing system to determine at least one of a dose set and a dose delivery. The sensing system is operable to detect relative rotational positions of first and second members of the device which are indicative of at least one of an amount of a dose set and an amount of a dose delivered by operation of the device, and generate outputs correlated to such relative rotational positions. The system includes a wiper coupled to the first
(Continued)

member, and a sensing band coupled to the second member for physically contacting the wiper as the second member rotates relative to the first member. A controller electrically communicates with the sensing system to determine, based on the generated outputs of the sensing system, at least one of the amount of the dose set and the amount of the dose delivered by operation of the device.

22 Claims, 19 Drawing Sheets

(52) U.S. Cl.
CPC .... *A61M 5/31528* (2013.01); *A61M 5/31546* (2013.01); *A61M 5/31551* (2013.01); *A61M 2005/3125* (2013.01); *A61M 2005/3126* (2013.01); *A61M 2205/3317* (2013.01); *A61M 2205/3561* (2013.01); *A61M 2205/3569* (2013.01)

(56) References Cited

U.S. PATENT DOCUMENTS

| | | | |
|---|---|---|---|
| 2,853,586 A | 9/1958 | Vercesi | |
| 3,264,560 A * | 8/1966 | Cheney | H01H 36/0006 340/672 |
| 3,399,368 A | 8/1968 | Elliott et al. | |
| 3,723,061 A | 3/1973 | Stahl | |
| 4,315,252 A | 2/1982 | Tagami | |
| 4,486,891 A | 12/1984 | Kimoto et al. | |
| 4,529,401 A | 7/1985 | Leslie et al. | |
| 4,552,055 A | 11/1985 | Foxwell | |
| 4,592,745 A | 6/1986 | Rex et al. | |
| 4,865,591 A | 9/1989 | Sams | |
| 4,883,472 A | 11/1989 | Michel | |
| 4,931,041 A | 6/1990 | Faeser | |
| 5,279,586 A | 1/1994 | Balkwill | |
| 5,418,362 A | 5/1995 | Lusby et al. | |
| 5,509,905 A | 4/1996 | Michel | |
| 5,536,249 A | 7/1996 | Castellano et al. | |
| 5,569,212 A | 10/1996 | Brown | |
| 5,582,598 A | 12/1996 | Chanoch | |
| 5,593,390 A | 1/1997 | Castellano et al. | |
| 5,626,566 A | 5/1997 | Petersen et al. | |
| 5,628,309 A | 5/1997 | Brown | |
| 5,674,204 A | 10/1997 | Chanoch | |
| 5,688,251 A | 11/1997 | Chanoch | |
| 5,691,646 A | 11/1997 | Sasaki | |
| 5,704,922 A | 1/1998 | Brown | |
| 5,728,074 A | 3/1998 | Castellano et al. | |
| 5,743,889 A | 4/1998 | Sams | |
| 5,820,602 A | 10/1998 | Kovelman et al. | |
| 5,827,232 A | 10/1998 | Chanoch et al. | |
| 5,920,198 A | 7/1999 | Suzuki et al. | |
| 5,921,966 A | 7/1999 | Bendek et al. | |
| 5,925,021 A | 7/1999 | Castellano et al. | |
| 5,938,642 A | 8/1999 | Burroughs et al. | |
| 5,954,700 A | 9/1999 | Kovelman | |
| 5,957,896 A | 9/1999 | Bendek et al. | |
| 5,961,496 A | 10/1999 | Nielsen et al. | |
| 6,001,089 A | 12/1999 | Burroughs et al. | |
| 6,004,297 A | 12/1999 | Steenfeldt-Jensen et al. | |
| D425,990 S | 5/2000 | Gravel et al. | |
| 6,068,615 A | 5/2000 | Brown et al. | |
| 6,080,090 A | 6/2000 | Taylor et al. | |
| 6,110,152 A | 8/2000 | Kovelman | |
| 6,192,891 B1 | 2/2001 | Gravel et al. | |
| 6,221,046 B1 | 4/2001 | Burroughs et al. | |
| 6,221,053 B1 | 4/2001 | Walters et al. | |
| 6,235,004 B1 | 5/2001 | Steenfeldt-Jensen et al. | |
| 6,248,095 B1 | 6/2001 | Giambattista et al. | |
| 6,277,099 B1 | 8/2001 | Strowe et al. | |
| 6,302,855 B1 | 10/2001 | Lav et al. | |
| 6,340,357 B1 | 1/2002 | Poulsen et al. | |
| 6,482,185 B1 | 11/2002 | Hartmann | |
| 6,540,672 B1 | 4/2003 | Simonsen et al. | |
| 6,558,320 B1 | 5/2003 | Causey, III et al. | |
| 6,585,698 B1 | 7/2003 | Packman et al. | |
| 6,663,602 B2 | 12/2003 | Moller | |
| 6,781,522 B2 | 8/2004 | Sleva et al. | |
| 6,875,195 B2 | 4/2005 | Choi | |
| 7,138,806 B2 | 11/2006 | Gafner et al. | |
| 7,195,616 B2 | 3/2007 | Diller et al. | |
| 7,704,238 B2 | 4/2010 | Diller et al. | |
| 7,992,460 B2 | 8/2011 | Boehen et al. | |
| 8,049,519 B2 | 11/2011 | Nielsen et al. | |
| 8,197,449 B2 | 6/2012 | Nielsen et al. | |
| 8,529,520 B2 | 9/2013 | Daniel | |
| 8,556,865 B2 | 10/2013 | Krulevitch et al. | |
| 8,672,899 B2 | 3/2014 | Diller et al. | |
| 2001/0013774 A1 | 8/2001 | Noltemeyer et al. | |
| 2002/0013522 A1 | 1/2002 | Lav et al. | |
| 2002/0020654 A1 | 2/2002 | Eilersen | |
| 2002/0120235 A1 | 8/2002 | Enggaard | |
| 2002/0177923 A1 | 11/2002 | Steffen | |
| 2003/0006209 A1 | 1/2003 | Stefen et al. | |
| 2005/0182358 A1 | 8/2005 | Veit et al. | |
| 2005/0182360 A1 | 8/2005 | Yeandel et al. | |
| 2007/0123829 A1 | 5/2007 | Atterbury et al. | |
| 2008/0140018 A1 | 6/2008 | Enggaard | |
| 2009/0318865 A1 | 12/2009 | Moller et al. | |
| 2010/0106098 A1 | 4/2010 | Atterbury et al. | |
| 2011/0313397 A1* | 12/2011 | Gold | A61M 5/31551 604/211 |
| 2012/0238960 A1 | 9/2012 | Smith et al. | |
| 2013/0072897 A1 | 3/2013 | Day et al. | |
| 2013/0310756 A1 | 11/2013 | Whalley et al. | |
| 2014/0074041 A1 | 3/2014 | Pedersen et al. | |
| 2014/0194829 A1 | 7/2014 | Baek et al. | |
| 2014/0243750 A1 | 8/2014 | Larsen et al. | |
| 2015/0018775 A1 | 1/2015 | Groeschke et al. | |
| 2015/0174330 A1 | 6/2015 | Nagel et al. | |
| 2015/0320934 A1 | 11/2015 | Draper et al. | |
| 2015/0343152 A1* | 12/2015 | Butler | A61M 5/31568 604/207 |
| 2016/0008552 A1 | 1/2016 | Madsen et al. | |
| 2016/0136353 A1 | 5/2016 | Adams | |
| 2016/0259913 A1 | 9/2016 | Yu et al. | |
| 2016/0296702 A1 | 10/2016 | Rasmussen et al. | |
| 2016/0378951 A1 | 12/2016 | Gofman et al. | |
| 2017/0023204 A1 | 1/2017 | Takeuchi et al. | |
| 2017/0128674 A1 | 5/2017 | Butler et al. | |
| 2017/0189625 A1 | 7/2017 | Cirillo et al. | |
| 2017/0274148 A1 | 9/2017 | Mews et al. | |

FOREIGN PATENT DOCUMENTS

| | | |
|---|---|---|
| EP | 0519137 | 12/1992 |
| EP | 0581925 | 2/1994 |
| EP | 0615762 | 9/1994 |
| EP | 0778034 | 6/1997 |
| EP | 0937471 | 8/1999 |
| EP | 0937472 | 8/1999 |
| EP | 1043037 | 10/2000 |
| EP | 1074273 | 2/2001 |
| EP | 1095668 | 5/2001 |
| EP | 1240913 | 9/2002 |
| EP | 2060284 | 5/2009 |
| EP | 2468340 | 6/2012 |
| EP | 2692378 | 2/2014 |
| GB | 2309801 | 8/1997 |
| WO | 9009202 | 8/1990 |
| WO | 9619872 | 6/1996 |
| WO | 0041754 | 7/2000 |
| WO | 0077472 | 12/2000 |
| WO | 0110484 | 2/2001 |
| WO | 0156635 | 8/2001 |
| WO | 0159570 | 8/2001 |
| WO | 02064196 | 8/2002 |
| WO | 02092153 | 11/2002 |
| WO | 03009461 | 1/2003 |
| WO | 03015838 | 2/2003 |

(56) References Cited

FOREIGN PATENT DOCUMENTS

| | | |
|---|---|---|
| WO | 03005891 | 11/2003 |
| WO | 2006045525 | 5/2006 |
| WO | 2011064299 | 6/2011 |
| WO | 2012004298 | 1/2012 |
| WO | 2013010893 | 1/2013 |
| WO | 2013098421 | 7/2013 |
| WO | 2014037331 | 3/2014 |
| WO | 2014128157 | 8/2014 |
| WO | 2015002806 | 1/2015 |
| WO | 2015123688 | 8/2015 |
| WO | 2016180873 | 11/2016 |
| WO | 2017021226 | 2/2017 |
| WO | 2017092960 | 6/2017 |
| WO | 2017165207 | 9/2017 |
| WO | 2018031390 | 2/2018 |
| WO | 2018111708 | 6/2018 |
| WO | 2018111709 | 6/2018 |

OTHER PUBLICATIONS

Soft Pot potentiometers http://media.digikey.com/pdf/Data%20Sheets/Spectra%20Symbol/SP%20Series%20SoftPot.pdf.
Hoffman-Krippner potentiometers http://www.hoffmann-krippner.com/potentiometers-sensofoil.html.
State Electronics potentiometers http://www.potentiometers.com.
International Search Report pertaining to International Application No. PCT/US2017/065247; dated Mar. 27, 2018.
Written Opinion of the International Searching Authority pertaining to International Application No. PCT/US2017/065247; dated Mar. 27, 2018.

* cited by examiner

MEDICATION DELIVERY DEVICE WITH SENSING SYSTEM

BACKGROUND

The present disclosure pertains to medication delivery devices, and, in particular, to a sensing system in a medication delivery device.

A variety of medication delivery devices, including for example pen injectors, infusion pumps and syringes, are commonly used for periodic administration of medications. It is important that the proper amount of medication be supplied at these times as the health of the patient is at stake. In many instances, failure to accurately deliver the appropriate amount of medication may have serious implications for the patient.

The administration of a proper amount of medication requires that the actual dosing by the medication delivery device be accurate. The term "dosing" as used herein refers to two phases of administering a dose, namely, setting the dose amount and delivering the amount of the set dose.

Medication delivery devices often utilize mechanical systems in which various members rotate or translate relative to one another. In most instances, these relative movements between members are proportional to the dose amount set and/or delivered by operation of the device. Accordingly, the art has endeavored to provide reliable systems that accurately measure the relative movement of members of a medication delivery device in order to assess the dose set and/or delivered.

While useful, prior art sensing systems are not without their shortcomings. For instance, some sensing systems take up more space within a delivery device than is desirable, resulting in a delivery device that is more bulky or inconvenient to use, or in a delivery device that has to sacrifice one or more features to have room in a compact device for the sensing system. Some sensing systems use relatively expensive componentry, or may be overly complicated so as to adversely impact the cost of manufacture or potentially the system reliability.

Thus, it would be desirable to provide a medication delivery device with a sensing system that can overcome one or more of these and other shortcomings of the prior art.

BRIEF SUMMARY

In one form thereof, the present disclosure provides a medication delivery device including a first member and a second member rotatable relative to the first member about an axis of rotation in proportion to at least one of an amount of a dose set and an amount of a dose delivered by operation of the medication delivery device. A radially projected wiper is coupled to the first member. An electrically operable sensing band is coupled to the second member. The sensing band is arranged in a curved shape and radially disposed relative to and in contacting relationship with the wiper, wherein, during relative rotation between the first and second members. The sensing band is operable to generate outputs associated with the relative angular position of the wiper along an operational angular length of the sensing band that is indicative of relative rotational positions of the first and second members. A controller electrically is coupled with the sensing band to determine, based on the outputs generated by the sensing band, at least one of the amount of the dose set and the amount of the dose delivered by operation of the medication delivery device.

In another form, a medication delivery device includes a first member and a second member rotatable relative to the first member about an axis of rotation in proportion to an amount of a dose set by operation of the medication delivery device, and a third member and a fourth member rotatable relative to the third member about the axis of rotation in proportion to an amount of a dose delivered by operation of the medication delivery device. A first wiper is coupled to the first member and projecting in a radial direction, and a second wiper is coupled to the third member and projecting in a radial direction. An electrically operable first sensing band is coupled to the second member, and an electrically operable second sensing band is coupled to the fourth member. Each of the first and second sensing bands is arranged in a curved shape and radially disposed relative to and in a contacting relationship with the first and second wipers, respectively. During relative rotation between the first and second members and relative rotation between the third and fourth members, each of the first and second sensing bands is operable to generate outputs associated with the relative angular position of the corresponding first and second wipers along an operational angular length of the respective first and second sensing bands that is indicative of relative rotational positions of the first and second members and the third and fourth members. A controller is electrically coupled with each of the first and second sensing bands to determine, based on the outputs generated by the first and second sensing bands, the amount of the dose set and the amount of the dose delivered by operation of the medication delivery device.

In another form thereof, the present disclosure provides a medication delivery device for delivering medication from a cartridge having a barrel holding the medication between a movable plunger and an outlet. The device includes a main housing, a cartridge housing for holding the cartridge extending from the main housing, a drive member, and a dose delivery mechanism. The drive member includes a forward end for engaging the movable plunger, and has a length extending in an axial direction within the main housing. The dose delivery mechanism is for controlling advancement of the drive member forward within the main housing in the axial direction to move the movable plunger for delivering medication through the outlet. The dose delivery mechanism includes a first member rotatable relative to the main housing in proportion to one of an amount of a dose set and an amount of a dose delivered by operation of the medication delivery device. The first member is relatively rotatable to the main housing about an axis of rotation extending in the axial direction. A sensing system is provided and is operable to detect relative rotational positions of the first member and the main housing and generate outputs correlated to such relative rotational positions. The sensing system includes a first wiper and a first sensing band. The first wiper is coupled to the first member and projecting in a radial direction. The first sensing band is coupled to the main housing. The first sensing band is arranged in a curved shape around the axis of rotation and has a first operational angular length. The first sensing band is disposed in the radial direction inward or outward of the first wiper for a physical contact with the first wiper during rotation of the first member relative to the main housing. The first sensing band includes an electrical characteristic correlated with where along the first operational angular length the first sensing band is operationally engaged in the radial direction due to the physical contact with the first wiper. A controller is in electrical communication with the sensing system to determine, based on outputs of the sensing system, at least one of the amount of the dose set and the amount of the dose delivered by operation of the medication delivery device.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
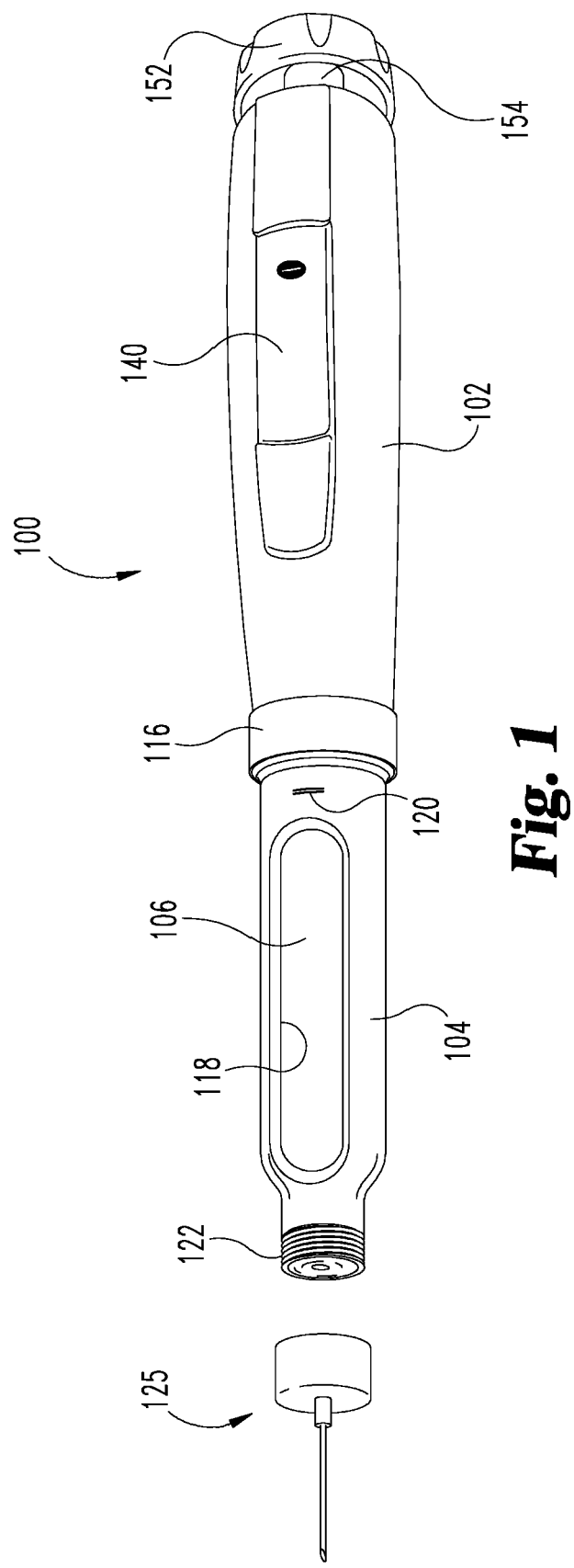
FIG. 1 is a perspective view of a medication delivery device in the form of an injection pen without a cap and prior to a mounting of a needle assembly.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Figure 2:
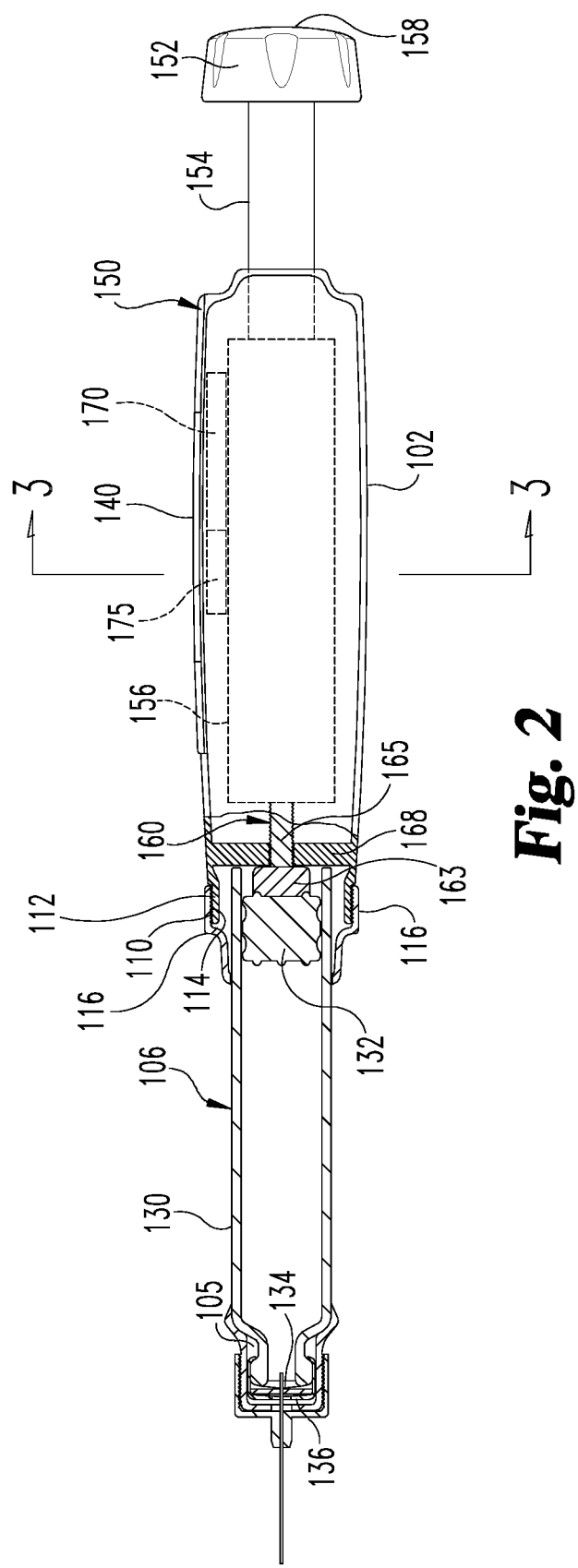
FIG. 2 is a side view in partial cross-section of the injection pen of FIG. 1 with a needle assembly attached and after a dose for delivery has been set.

Referring now to FIGS. 1-2, there is shown a medication delivery device equipped with a sensing system that is described further as being used to determine the amount of a dose set by operation of the device. Such amount is determined based on the sensing of relative rotational movements during dose setting between members of the medication delivery device, where the sensed movements are correlated as applicable to the amount of the dose set. In different embodiments, the sensing system is configured to determine the amount of at least one of the dose set and the dose delivered by operation of the device, or alternatively both the amount of the dose set and the amount of the dose delivered by operation of the device. One of the advantages of the disclosed embodiments is that a medication delivery device with sensing system may be provided that can accurately and reliably assess the amount of medication that has been set and/or delivered by that device. Another of the advantages is that a medication delivery device with sensing system may be provided that requires a limited number of individual parts. Still another of the advantages is that a medication delivery device with sensing system may be provided which has a compact form factor.

The shown device is a reusable pen-shaped medication injection device, generally designated 100, which is manually handled by a user to selectively set a dose and then to inject that set dose. The description of device 100 is merely illustrative as the sensing system can be adapted for use in variously configured medication delivery devices, including differently constructed pen-shaped medication injection devices, differently shaped injection devices, and infusion devices. The medication may be any of a type that may be delivered by such a medication delivery device. Device 100 is intended to be illustrative and not limiting as the sensing system described further below may be used in other differently configured devices. Device 100 is similar in many respects to a device described in U.S. Pat. No. 7,195,616, which is incorporated herein by reference in its entirety.

As used herein, the term "coupled" encompasses any manner by which a first item is caused to move in unison with or in proportion to a second item as the second item moves. Items are rotationally coupled if they are caused to rotate together. Coupling systems may include, for example, connections provided through splines, gears or frictional engagement between the members, or similar connections provided by other components which indirectly couple the members. Where applicable, an item may be coupled to another item by being directly positioned on, received within, attached to, or integral with the other item, or otherwise secured thereto, directly or indirectly.

The term "fixed" is used to denote that the indicated movement either can or cannot occur. For example, a first member is "rotatably fixed with" or "fixed against rotation relative to" a second member if the first member is not able to rotate relative to the second member.

Medication injection device 100 includes an outer housing that supports the internal components of the device. The housing is shown as having a rear or main housing 102 and a forward or cartridge housing 104. Main housing 102 is configured to hold a drive assembly of the device, which assembly is a strictly user powered, mechanical assembly as described but may in alternate embodiments be a motorized assembly. Cartridge housing 104, also known as the cartridge retainer, holds a cartridge 106 filled with medication to be delivered by device operation. Cartridge retainer 104 is detachably connectable or mountable to main housing 102 via external threading 110 on a protruding collar portion 112 of main housing 102 which mates with internal threading 114 on a ring portion 116 at the proximal end of cartridge retainer 104. Suitable detachable connecting elements other than threadings 110 and 114 are known in the art and naturally may be employed, such as a bayonet fitting, or the use of an additional latching component.

Cartridge retainer 104 includes an internal hollow 105 suited to removably receive cartridge 106, thereby allowing a cartridge to be inserted therein, and then removed therefrom when depleted and replaced with a fresh cartridge of similar design. Openings 118 in cartridge retainer 104 allow visibility of the cartridge contents. A detent feature 120 provided on the exterior of cartridge retainer 104 allows for a not shown protective cap to be detachably mounted over the cartridge retainer 104 when a needle assembly 125 is not attached to the cartridge retainer 104. Although cartridge retainer 104 is described herein as being a reusable component, the cartridge retainer 104 can be integrated with, and therefore be disposable with, the cartridge 106.

Medication cartridge 106 is of conventional design, including a barrel 130 having an interior reservoir filled with medication which is sealed at one end by a slidable plunger or piston 132 and sealed at the other end by a septum 134 held by a crimp ring 136.

A needle assembly 125 detachably mountable to an externally threaded distal end 122 of cartridge retainer 104 pierces the septum 134 when so mounted. The pierced septum through which the needle extends serves as an outlet during dispensing for the medication within the reservoir of barrel 130, which medication is delivered through the needle assembly 125 by operation of device 100. The cartridge 106 can hold multiple doses of medication, or even a single dose, depending on the purpose of device 100.

Medication injection device 100 is shown in FIG. 1 in its "zero position" at which the device has not been set for delivery of any dose. This zero position setting is indicated by the number "0" visible somewhere on the device, such as, for example, on an electronic dose display 140 in FIG. 1. In FIG. 2, device 100 is arranged after being manipulated to set a dose of thirty units for delivery, and the number "30" would be visible, such as, for example, on the display 140.

Medication injection device 100 is typical of many such reusable devices including a manually-powered dose delivery mechanism, generally designated 150, that controls forward or distal advancement of a drive member, generally designated 160. Drive member 160 advances within the cartridge barrel 130 to directly engage and advance plunger 132. As shown in FIG. 2, dose delivery mechanism 150 includes a dose knob 152 connected via a tube 154 to a mechanical drive assembly abstractly indicated at 156 that is housed within main housing 102. When knob 152 is turned by a user to set a dose for injection, dose knob 152 and tube 154 screw out together proximally from main housing 102. When a user applies a plunging distal force on the proximal end 158 of dose knob 152, the resulting purely translational axial motion of dose knob 152 and tube 154 distally forward into main housing 102 is converted by drive assembly 156 into a smaller motion of drive member 160 forward from main housing 102 into the interior of cartridge barrel 130.

Drive member 160 is formed in two pieces including a forward end 163 that directly engages the cartridge plunger 132, and a shaft 165 that axially extends rearward from forward end 163 into main housing 102. The shaft 165 is threaded and is engaged with drive assembly 156 to be screwed out from main housing 102 and thereby driven forward. Shaft 165 is shown threadedly engaged with a housing bulkhead 168, which housing bulkhead is shown integral with main housing 102 but can be separately formed and fixedly attached thereto. Forward end 163 is provided in the form of an enlarged foot that is mounted on shaft 165 to allow relative rotation, allowing foot 163 to engage plunger 132 without relative rotation therebetween as shaft 165 screws out. While this foot and shaft two-piece construction of drive member 160 is preferred when shaft 165 screws out from the housing during advancement, such a construction is not required in devices, particularly if the drive member simply translates as it is forced forward from the housing, in which case a single piece drive member construction may be more acceptable.

Device 100 uses an electronic dose display 140 rather than a helically marked dial display as used in many other reusable injection devices. Display 140 is circuited to and controlled by an electronic controller or computing assembly 170 mounted within main housing 102. Controller 170 can include conventional components such as a processor, power supply, memory, etc. Controller 170 is programmed to achieve the electronic features of device 100, including causing the display of set doses. The set dose displayed in display 140 is determined by the interaction of dose delivery mechanism 150 with a sensing system, abstractly shown at 175, which is electrically circuited with controller 170.

Figure 3:
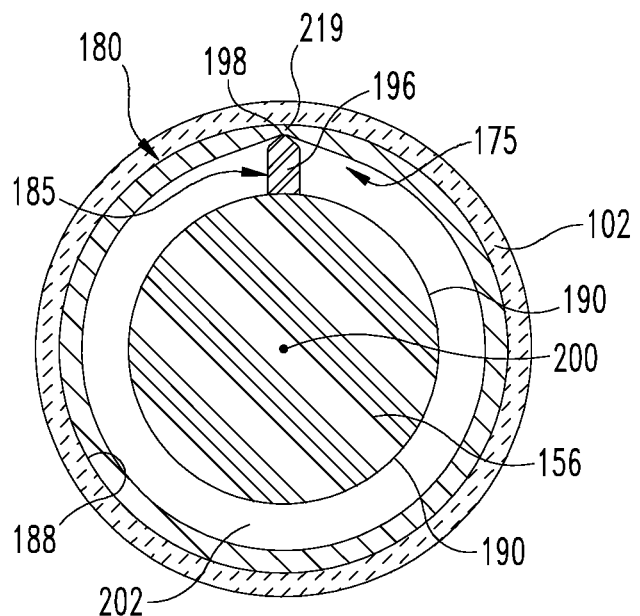
FIG. 3 is an abstract cross-sectional view taken along line 3-3 of FIG. 2 further showing a sensing system.
Figure 4:
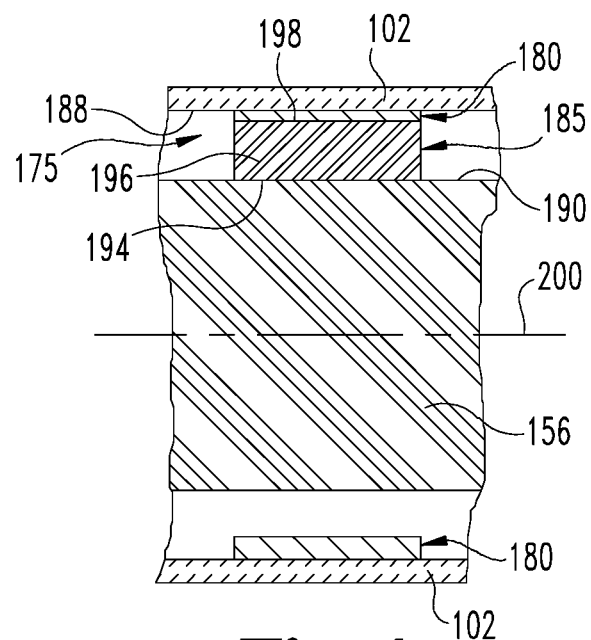
FIG. 4 is a partial, abstract cross-sectional side view of the injection pen of FIG. 1.
Figure 5:
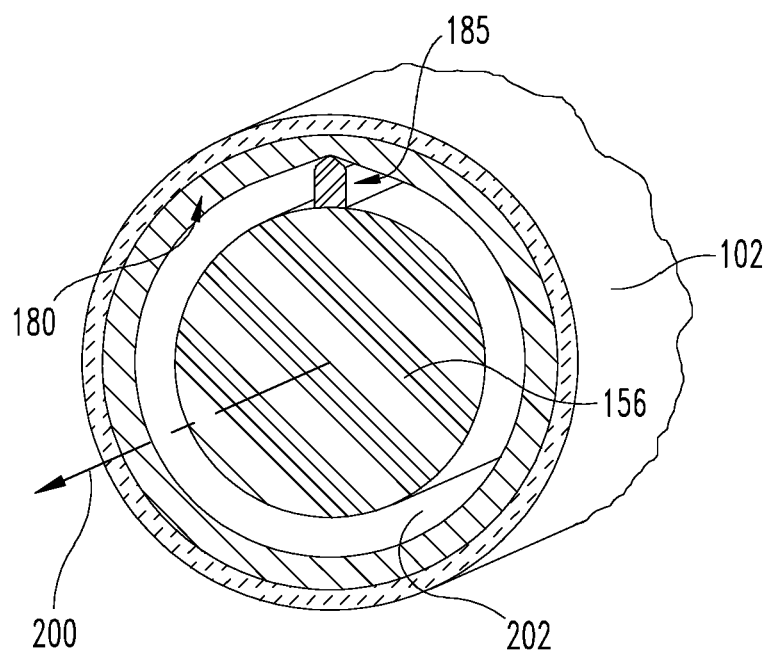
FIG. 5 is a perspective view of FIG. 3.

With additional reference to FIGS. 3-5, sensing system 175 is coupled to two members of device 100 which, when a dose is set by a user screwing dose knob 152 out from housing 102, are relatively rotatable in proportion to the amount of such set dose. Depending on the configuration of device 100 and in particular the drive assembly 156, those two members of device 100 to which sensing system 175 is coupled also can be rotatable relative to each in proportion to the amount of a dose delivered by plunging operation of dose knob 152, and in which case sensing system 175 can additionally be used in determining the delivered dose. Alternatively, in another embodiment where dose delivered instead of dose set is sensed, sensing system 175 is positioned for sensing dose delivered by being coupled to two members of device 100 which, during dose delivery, are relatively rotatable in proportion to the amount of dose delivered, but which two members do not relatively rotate during dose setting.

Sensing system 175 operates to detect relative rotational positions of the first and second device members to which it is coupled and generates outputs correlated to such relative rotational positions. Sensing system 175 includes a sensing band 180 and a wiper 185. In device 100, sensing band 180 is coupled to housing 102, and wiper 185 is coupled to a part of drive assembly 156 that at select times of device use rotates within the housing interior. Sensing band 180 alternatively can be coupled to housing 102 via one or more intermediate components, and further alternatively can be coupled to housing 102, either directly or directly, to not rotate relative to the housing but be free to move axially, such as if the wiper 185 with which it engages moves axially during device use and sensing band 180 were attached directly to a component rotatably fixedly, and axially movably, mounted to the housing 102.

As abstractly shown in FIG. 3, sensing band 180 is directly attached, such as with an adhesive, to the interior circumferential and radially inwardly facing surface 188 of housing 102, while wiper 185 is directly attached, such as with an adhesive or by being integrally formed therewith, to an outer radial surface 190 of a part of the drive assembly 156. Drive assembly 156 can take various forms, but typically involves multiple interacting parts, and wiper 185 is shown positioned on a rotatable part of this assembly so as to have direct contacting access to the sensing band 180.

Wiper 185 includes a body 196 that projects radially outward from its inward end 194 to its outward end 198. Outward end 198 has a rounded apex that provides a precise point of contact for sliding engagement with sensing band 180 along the circumferential extent of the band. Wiper body 196 has an axially extending length parallel to the axis of rotation, indicated at 200, about which rotates the part of the drive assembly 156 from which the wiper projects. As no electrical current is routed through it, wiper 185 can be formed entirely of an electrically non-conductive material such as a thermoplastic elastomer such as silicone.

The wiper alternatively can be a single point contact, without the axial length as shown. The wiper need not extend the width, as extending in the axial direction, of the resistor strip within sensing band 180. Providing wiper 185 with an axial length can account for both tolerances within the design of the device as well as axial motion within the device of the wiper 185 relative to the sensing band 180 and housing 102.

The radial height of wiper body 185 is designed to span the annular space or gap 202 within the housing interior between sensing band 180 and drive assembly 156. Wiper 185 projects sufficiently far radially outward to provide at least a minimum application force and thereby operationally engage sensing band 180 as described further below. Such force can be controlled by the manufacturer through the material selection and processing, such as tempering, as well as the geometry of the wiper and its residual compression within 156. To better ensure a proper engagement with sensing band 180 at all angular positions of the drive assembly 156, and thereby wiper 185, relative to housing 102, wiper 185 can be biased radially outward from drive assembly 156. Such a biasing can be provided by a material resiliency resulting from forming wiper 185 out of a durable but elastic material such as a thermoplastic elastomer or butyl rubber with a suitable durometer. The biasing can also or alternatively be provided by an additional spring element acting in a radial direction between wiper 185 and drive assembly 156. Still further, a biasing of the sensing bands radially inwardly, such as by placing spring elements to act radially between the outer radial periphery of the sensing bands and the housing radial interior surface, can be done alternatively or additionally.

Wiper 185 and sensing band 180 are in radial alignment when active to sense relative rotational positions. In device embodiments where for example the drive assembly 156 moves axially from one state, where the sensing system 175 is not used, to a second state, at which the sensing system 175 is used, the wiper 185 and sensing band 180 can be axially spaced when not being used.

Other wiper shapes than the one shown in FIG. 3 can be used to activate sensing band 180. Such additional wiper shapes include round protrusions, or journaled disks or cylinders that result in rolling contact with sensing band 180.

Sensing band 180 is configured to generate an electrical output based on where along its angularly extending operational length it is directly contacted by wiper 185. Sensing band 180 is arranged within housing 102 in a curved shape around axis of rotation 200, and the band is disposed radially outward of wiper 185. Sensing band 180 is shown in FIG. 3 as being annular in shape to extend the full 360 degrees of the housing internal circumference and completely ring the axis of rotation 200. Alternatively, sensing band 180 can be in a ring shape that does not completely encircle or ring the axis of rotation.

Figure 6:
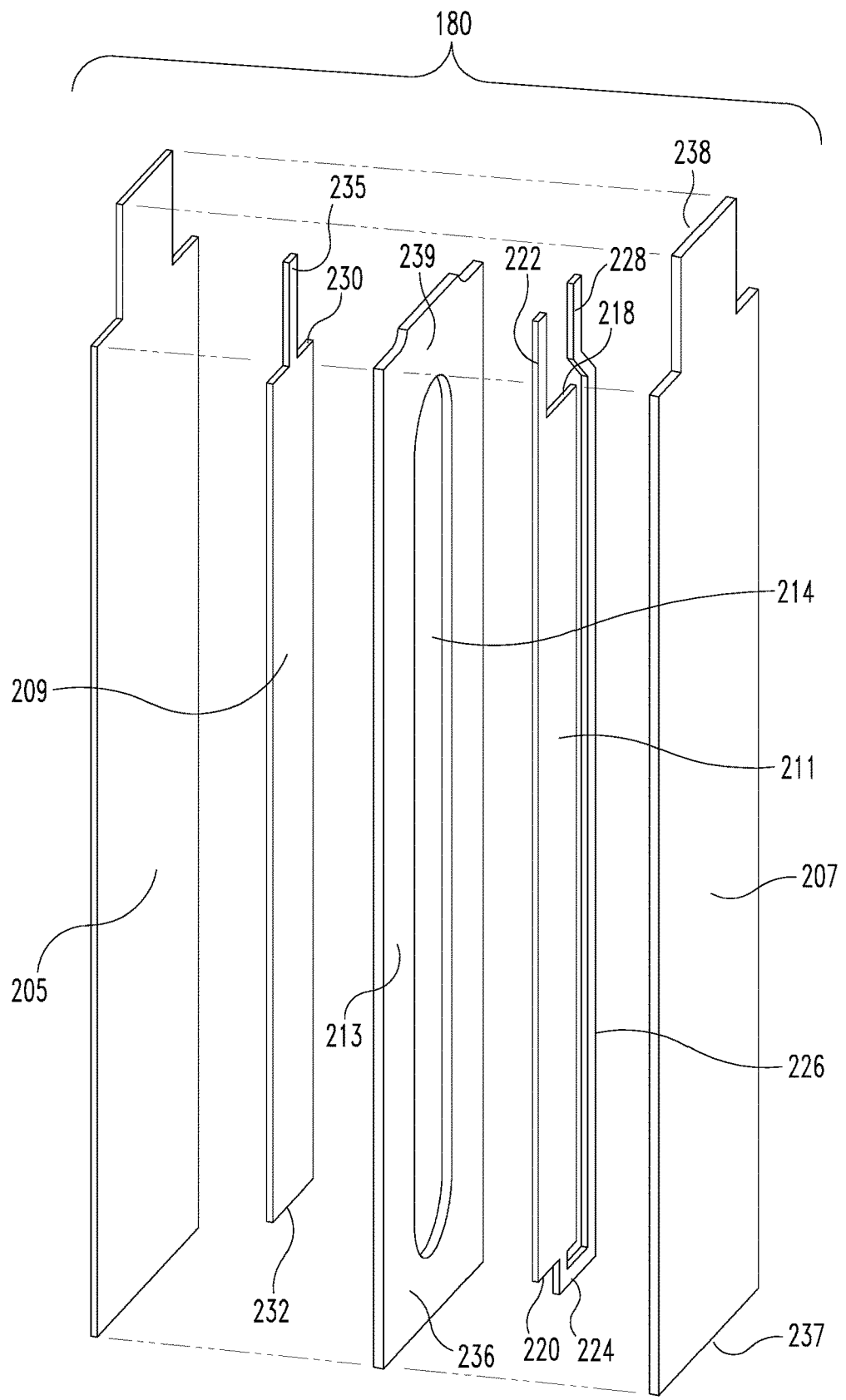
FIG. 6 is an exploded perspective view of the sensing band of the sensing system in an uncurved, or straight, configuration.

Sensing band 180 can be formed by a membrane potentiometer manufactured in the curved shape to facilitate assembly within device 100 to remove residual stresses. One suitable sensing band is available from Tekscan Incorporated. The membrane potentiometer is an assembly of components that are abstractly shown in an uncurved state in FIG. 6, but descriptions of radial and angular refer to the sensing band in the rounded configuration shown in the other figures. The sensing band 180 includes first and second substrates or backing strips 205, 207, and first and second electrical strips 209 and 211 that sandwich a spacer 213. Substrates 205 and 207, and spacer 213, are made of a pliable plastic that is electrically non-conductive such as PET (polyethylene terephthalate) or a polymide film such as Kapton. Alternatively, spacer 213 can be a printed material deposited directly onto either substrate 205 or 207 by means such as screen printing. Spacer 213, which serves to keep the electrical strips 209 and 211 apart absent a sufficient force applied by the wiper, can also have an adhesive property to connect the substrates 205 and 207 together. Substrates 205 and 207 and the outer edges of spacer 213 form the exterior of sensing band 180, and, when sealed together along their peripheral regions, protectively encase strips 209 and 211. Strips 209 and 211 are secured to the substrates 205 and 207 and/or the spacer 213, or can be otherwise formed such as screen printed, for example, directly to the substrates.

Electrical strips 209 and 211 when in a neutral state are held within sensing band 180 in spaced relationship due to the interposition of spacer 213. When band 180 is in its curved configuration within device 100, strip 209 is disposed radially inward of strip 211, and absent an external force the strips 209 and 211 are radially spaced resulting in no electrical connection therebetween. In this radially spaced relationship, strips 209 and 211 are directly facing each other through the central slot-shaped opening 214 within spacer 213. Not shown dielectric projections also can be provided on one of the electrical strips 209 or 211 within opening 214 to ensure the strips 209 and 211 remain so radially spaced absent a wiper induced movement. Such projections can be provided, such as by screen or jet printing, in any suitable pattern that maintains the strip radial spacing, such as discrete bumps arranged in a polka dot pattern, parallel ribs oriented axially that span the strip width and which are spaced from each other along the length of the strip, parallel ribs oriented at an angle relative to the strip width which span that strip width and which are spaced from each other along the length of the strip, or parallel ribs oriented circumferentially that span the strip length and which are spaced from each other along the width of the strip.

Electrical strip 211 is an electrical resistor element that has an electrical resistance that varies linearly along its length that extends from a first angular end 218 to a second angular end 220. A first electrical lead 222 is circuited with and extends from end 218, and a second electrical lead 224 is circuited with and extends from end 220. Lead 224 is routed at 226 near the electrical strip side to a lead end 228 parallel to lead 222 which facilitates the electrical connection of sensing band 180 with the device circuitry.

Electrical strip 209 is an electrical conductor element with very low electrical resistance, such as made of silver, copper or gold, having a length that extends from a first angular end 230 to a second angular end 232. A first electrical lead 235 is circuited with and extends from end 230.

While leads 235, 222 and 228 are shown as positioned in an extension of the substrates 205 and 207 that extends in the angular direction along the lengths of such substrates, in an alternate embodiment such leads can be routed to an alternate substrate portion that alternatively or additionally extends laterally, or in the axial direction, from the substrates to facilitate an electrical connection.

Strip 209 is sufficiently flexible along its length to allow its deflection in the outward radial direction, at the point where it is acted upon, through the substrate 205, by wiper 185, to be in direct physical and electrical contact with electrical strip 211. This wiper causes a compression, indicated at 219 in FIG. 3, that deflects strip 209 radially outward thereat to result in wiper 185 operationally engaging the sensing band 180 by causing an electrical contact between strips 209 and 211 thereat, but with the strips otherwise remaining radially spaced. The resistance between electrical leads 235 and 222 varies linearly with the distance between the angular end 218 and the point of contact between strips 209 and 211. The resistance between electrical leads 235 and 228 varies linearly with the distance between the second angular end 220 and the point of contact between strips 209 and 211. The resistance between the electrical leads 222 and 228 is equal to the sum of the electrical resistance between leads 235 and 222 plus the resistance between leads 235 and 228.

In an alternate embodiment, and provided resistor element 211 has flexibility properties similar to that of conductor element 209 to allow a deflection by wiper engagement, sensing band 180 can be configured to have resistor element 211 be radially inward of conductor element 209 in the shown device 100.

Figure 7:
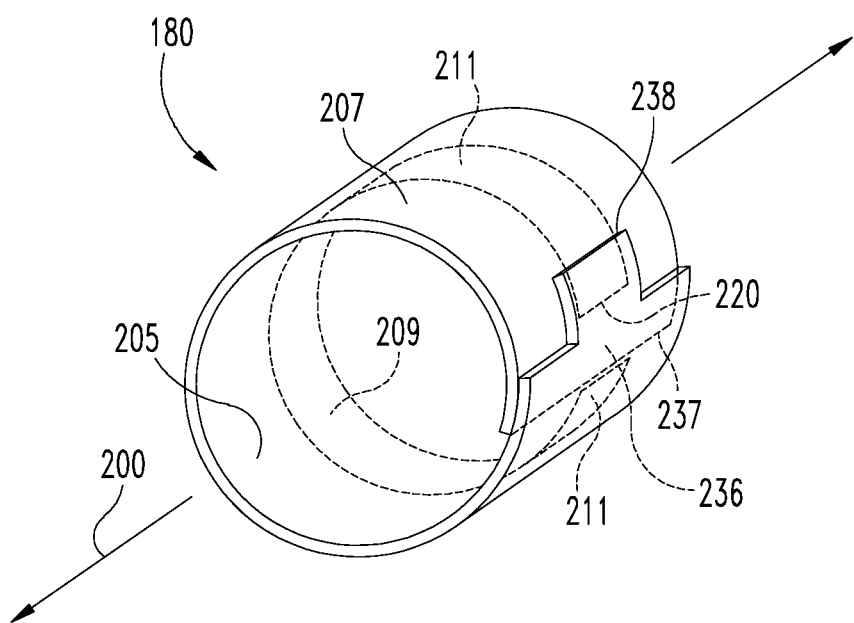
FIG. 7 is a perspective view of the sensing band of FIG. 6 in a ring-shaped configuration.

Sensing band 180 is shown in FIG. 7 removed from the remainder of device 100. Sensing band 180 is exactly circumferentially wrapped around the axis of rotation 200 so as to minimize the use of axial space within device 100 devoted to sensing system 175. Band 180 can alternatively have its ends axially offset so that band 180 is arranged as a helix. Sensing band 180 is operational to sense wiper 185 at any point along the angular length of sensing band 180 at which electrical strips 209 and 211 are present and capable of being brought into electrical contact by a radial deflection caused by wiper 185. Sensing band 180 has an electrical characteristic correlated with where along its angular operational length it is operationally engaged due to the physical contact with wiper 185.

For the shown embodiment, the angular operational length of sensing band 180 for which sensing is effective is less than 360 degrees around the axis of rotation 200 for the wrapping of the band 180. This length is due to end region 236 of spacer 213 proximate the first end 237 of band 180, at which region there is no sensing. This spacer end region 236 is overlapped by the opposite second end 238 of band 180, with sensing band 180 being sized such that effective portions of electrical strips 209 and 211 proximate the opposite end region 239 of spacer 213, while not angularly overlapping spacer end region 236, stop immediately before such an overlapping as shown in FIG. 7. As a result, the operational angular length extends less than 360 degrees around the housing inner circumference, and in particular 360 degrees minus the portion of the inner circumference spanned by the spacer end region 236. One suitable operational length extends at least 345 degrees. In an alternate embodiment in which a sensing band 180 is longer, the effective length of the electrical strips 209 and 211 can overlap end region 236.

Figure 8:
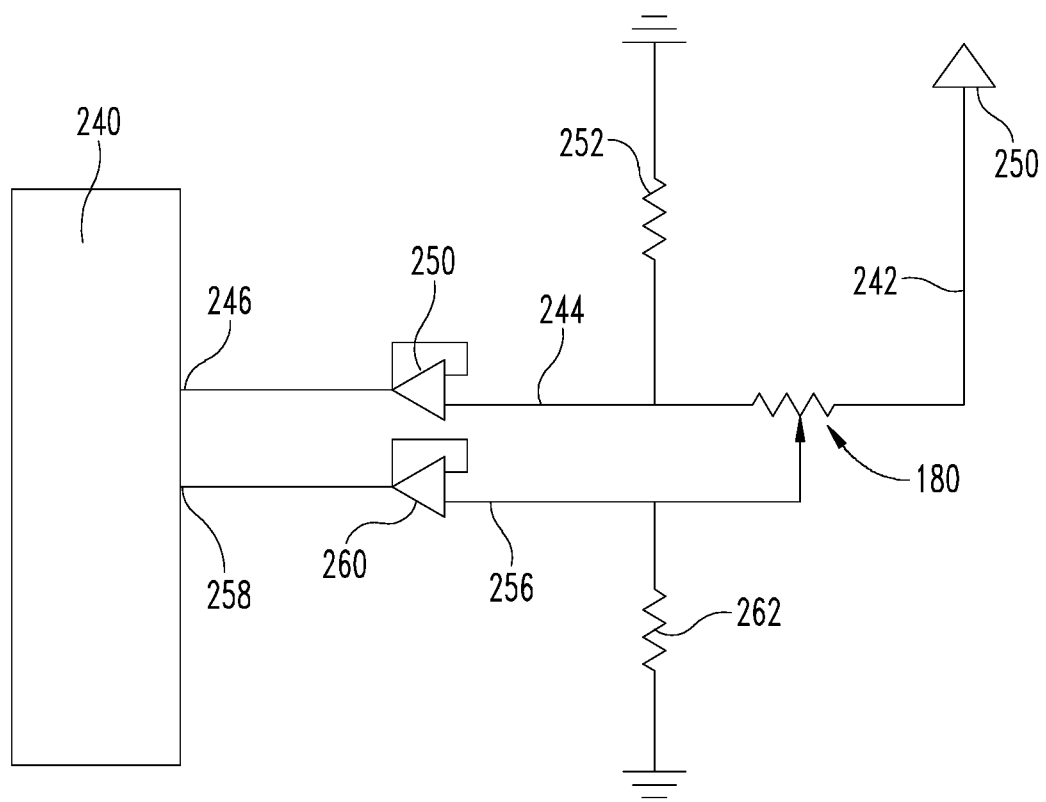
FIG. 8 is a schematic of an electrical circuiting of the sensing system with the controller microprocessor.

Controller 170 includes a microprocessor 240 electrically circuited with sensing band 180 as shown schematically in FIG. 8. The electrical outputs from the sensing band 180 that reach microprocessor 240 are processed by the microprocessor to identify the amount of the dose set by operation of the device 100, specifically based on the microprocessor 240 determining relevant movement of the drive assembly 156 relative to the main housing 102 during dose setting.

As represented in FIG. 8, an electrical power source 250, such as a 1.8 volt source, that is housed within device 100 within controller 270 is circuited at node 242 with lead 222 from resistor element 211 which acts as an input to sensing band 180. The output lead end 235 of conductor element 209 is circuited at node 256 to an input port 258 of the electrically grounded microprocessor 240 through a signal amplifier 260. Node 256 is grounded through a voltage divider resistor 262 to provide a voltage to the microprocessor 240 that is proportional to the resistance between nodes 256 and 242. The output lead 228 of resistor element 211 is circuited at node 244 to a second input port 246 of the electrically grounded microprocessor 240 through signal amplifier 250, and node 244 is grounded through a voltage divider resistor 252 to provide a voltage to the microprocessor 240 that is proportional to the resistance between nodes 244 and 242.

Due to the voltage signal received by microprocessor 240 via node 256 being dependent on where along the angular length of resistor element 211 the wiper 185 has caused resistor element 211 to be contacted by the deflection of conductor element 209, controller 170 can determine the relative positions of the members sensed by sensing system 175, namely the drive assembly 156 and the housing 102.

The shown circuitry results in a differential voltage signal being provided at inputs 246 and 258 to the microprocessor 240 that can be used to compensate for any variations in the output of sensing band 180 that can occur over time or due to environmental conditions. Such a circuitry differential signal can not be required with a sensing band in an alternate embodiment.

The operational angular length of sensing band 180 being less than three hundred sixty degrees results in a sensing gap around the housing inner circumference. Unless the wiper has an angular length larger than the sensing gap, there is time during the circumferential travel of the wiper that the presence of wiper 185 cannot be actually sensed by the sensing system 175. The controller 170 can be programmed to understand that sensing system 175 not outputting a wiper engagement in fact corresponds to wiper 185 being aligned with the sensing gap. If such a programming is not desired, or if the sensing gap is larger than the angular resolution needed for a particular application, an alternate sensing system can be employed.

Figure 9:
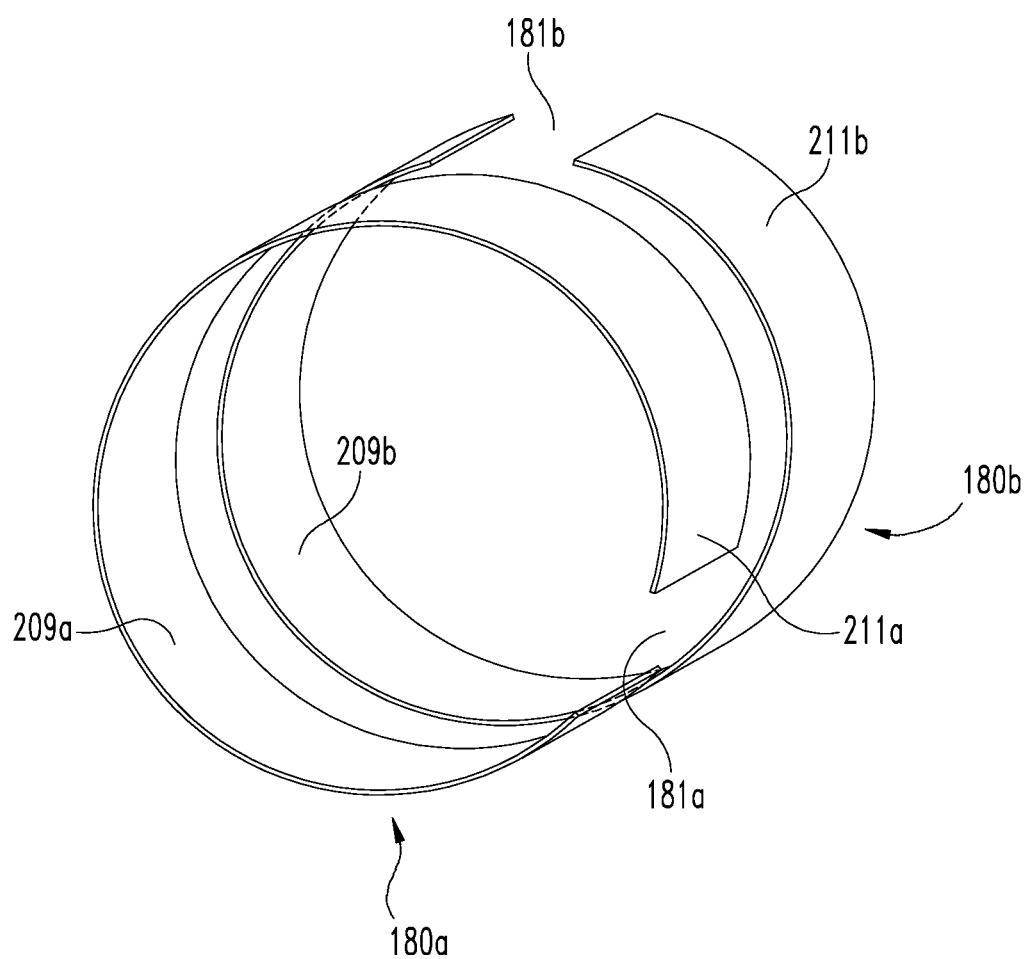
FIG. 9 is an abstract perspective view of another configuration of sensing bands of a sensing system.
Figure 10:
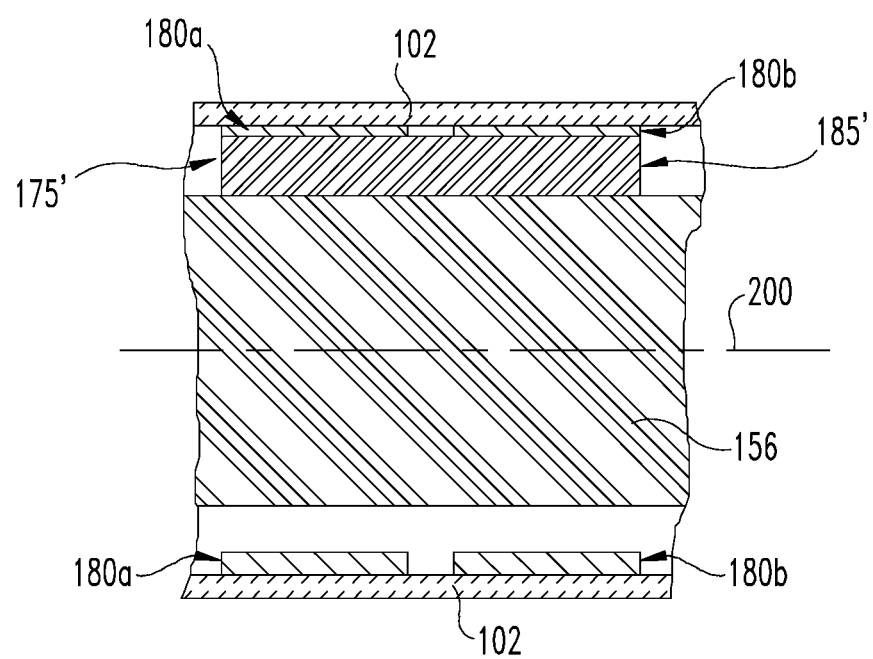
FIG. 10 is a partial, abstract cross-sectional view similar to FIG. 4 of the sensing system bands of FIG. 9 and a suitable wiper installed in the device of FIG. 1.

One such alternate sensing system is abstractly shown in pertinent part in FIGS. 9 and 10. The sensing system, generally designated 175', can be used in place of sensing system 175 in device 100 to sense the relative positions of housing 102 and drive assembly 156. Sensing system 175' includes first and second sensing bands 180a and 180b each the same structurally as sensing band 180 with electrical circuiting to the device controller but not each other. Sensing bands 180a and 180b are coaxially arranged and each is in an exact circumferential arrangement around axis of rotation 200. Sensing bands 180a and 180b are closely spaced axially with the electrical strips of each band 180a and 180b not being in an axially overlapping relationship with the electrical strips of the other.

Sensing band 180a includes a resistor element 211a and a conductor element 209a, while sensing band 180b includes a resistor element 211b and a conductor element 209b. The angular operative length of each band 180a and 180b is shown in FIG. 9 as being the same as band 180, and each of such lengths extends only partially around a circumference of the drive assembly 156. Such a configuration results in sensing band 180a having a sensing circumferential gap 181a and sensing band 180b having a sensing circumferential gap 181b. While the operative lengths of bands 180a and 180b are shown as being equal, such is not required so long as one sensing band covers the sensing circumferential gap of the other.

The wiper of sensing system 175' is shown as a single, axially extending element 185' that engages both sensing bands 180a and 180b. Different axial regions of wiper 185' engage different sensing bands 180a and 180b. In a not shown alternate embodiment, the wiper need not be a single continuous member as shown in FIG. 10 but instead can be two distinct wipers, or can have an interruption along its axial length which does not interfere with the operation of engaging the sensing bands 180a and 180b as appropriate.

Sensing bands 180a and 180b are angularly staggered as shown in FIG. 9 such that sensing circumferential gaps 181a and 181b do not line up at all axially. As a result, when wiper 185' is oriented so as to be located within angular gap 181a it will simultaneously and necessarily be engaging sensing band 180b and not be positioned so as to try to operationally engage within gap 181b. Controller 170 is programmed to understand from the combination of outputs from sensing bands 180a and 180b where the wiper 185', and therefore the drive assembly 156, is located relative to the housing 102. The controller 170 can also use the combination of outputs to determine if one of the sensing bands is not operating correctly.

Sensing bands 180a and 180b are shown in FIGS. 9 and 10 as being separately formed and positioned within a device. In an alternate construction, the resistor elements, conductor elements and leads of the shown two sensing bands can all be provided on appropriately sized and shaped, common substrates, and with an appropriate common spacer. This construction results in a single sensing band, with two sets of angularly staggered resistor and conductor elements, each set with their own electrical contacts for circuiting to the device controller but not the other set, which can be handled as a single unit.

In a still further alternate embodiment which is not shown, the sensing circumferential gaps of the two, or even more, sensing bands can be axially aligned. However, the wiper element would have portions on different axial segments of the drive assembly 156, which wiper portions would be appropriately angularly spaced around the drive assembly 156 so as to not all simultaneously engage the sensing gaps of the multiple sensing bands.

Figure 11:
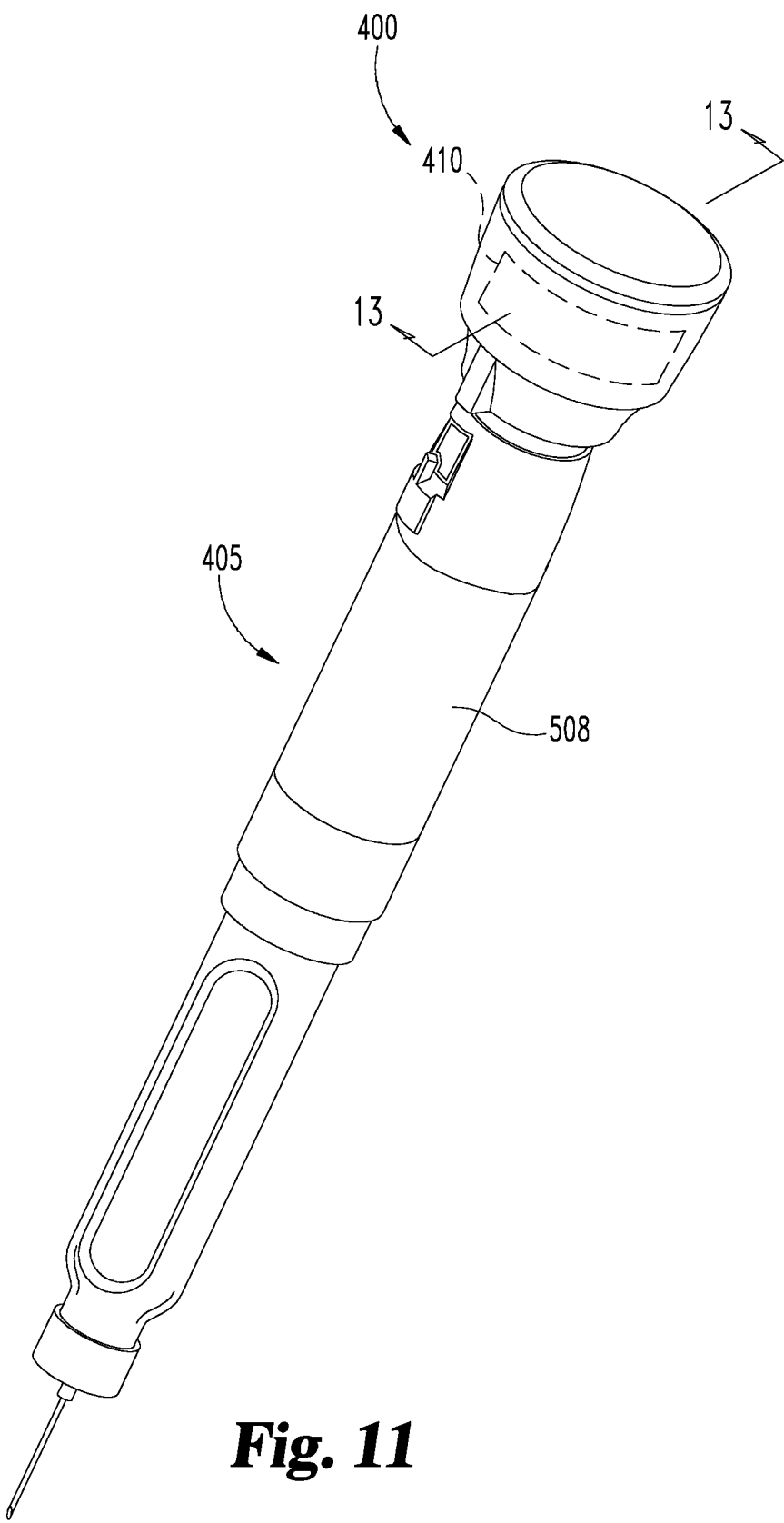
FIG. 11 is a perspective view of an alternate embodiment of a medication delivery device with sensing system.

Referring now to FIG. 11, there is shown in perspective view an alternate medication delivery device with sensing system. The sensing system is incorporated into a dose delivery detection module, generally designated 400, that is detachably mounted over the proximal end of the remaining portion of the delivery device, generally designated 405. When module 400 is mounted as shown, its sensing system abstractly represented at 410 in FIG. 11 detects relative rotational positions of module housing parts, and thereby relative rotational positions of first and second members of device portion 405, during dose delivery and generates outputs correlated to such relative rotational positions which are used by controller 415 to identify the dose delivered by operation of the device.

Figure 12:
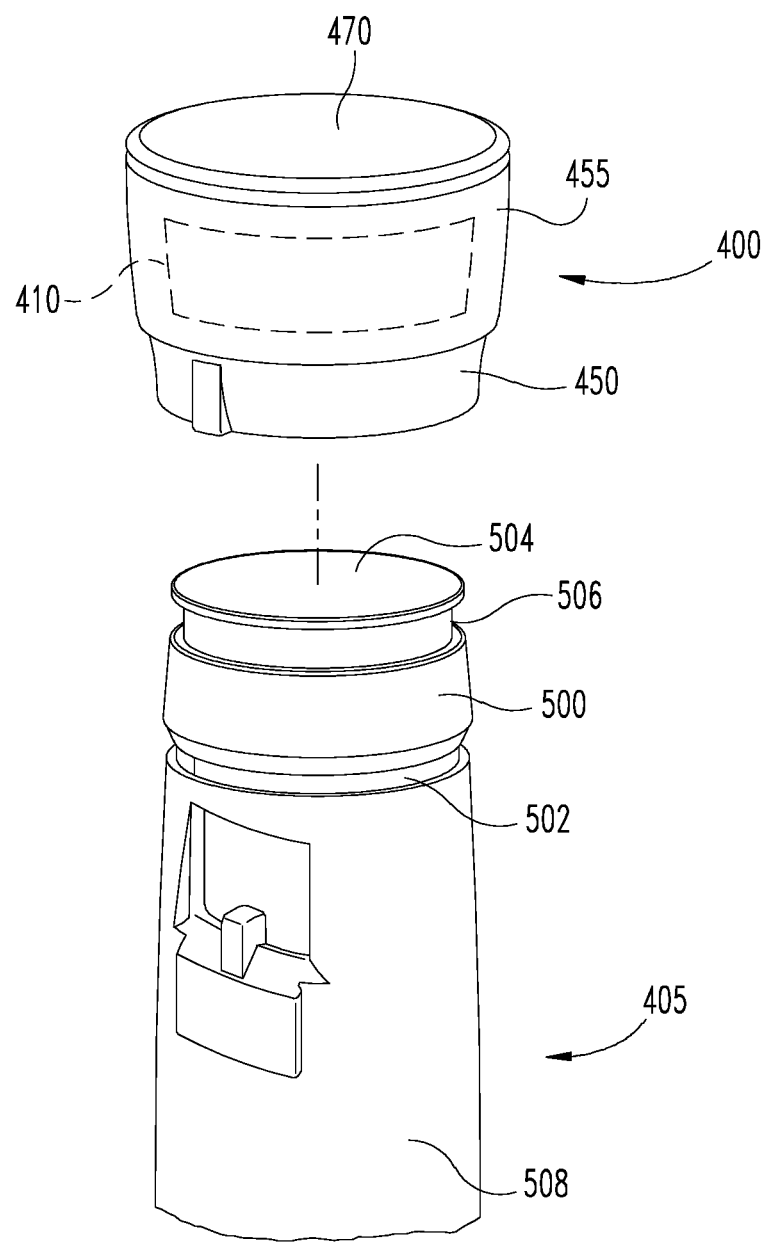
FIG. 12 is a partial perspective view of the device of FIG. 11 showing the dose delivery detection module detached from the remainder of the device.

FIG. 12 shows module 400 either prior to its releasable mounting to device portion 405, or after having been demounted from device portion 405.

Figure 13:
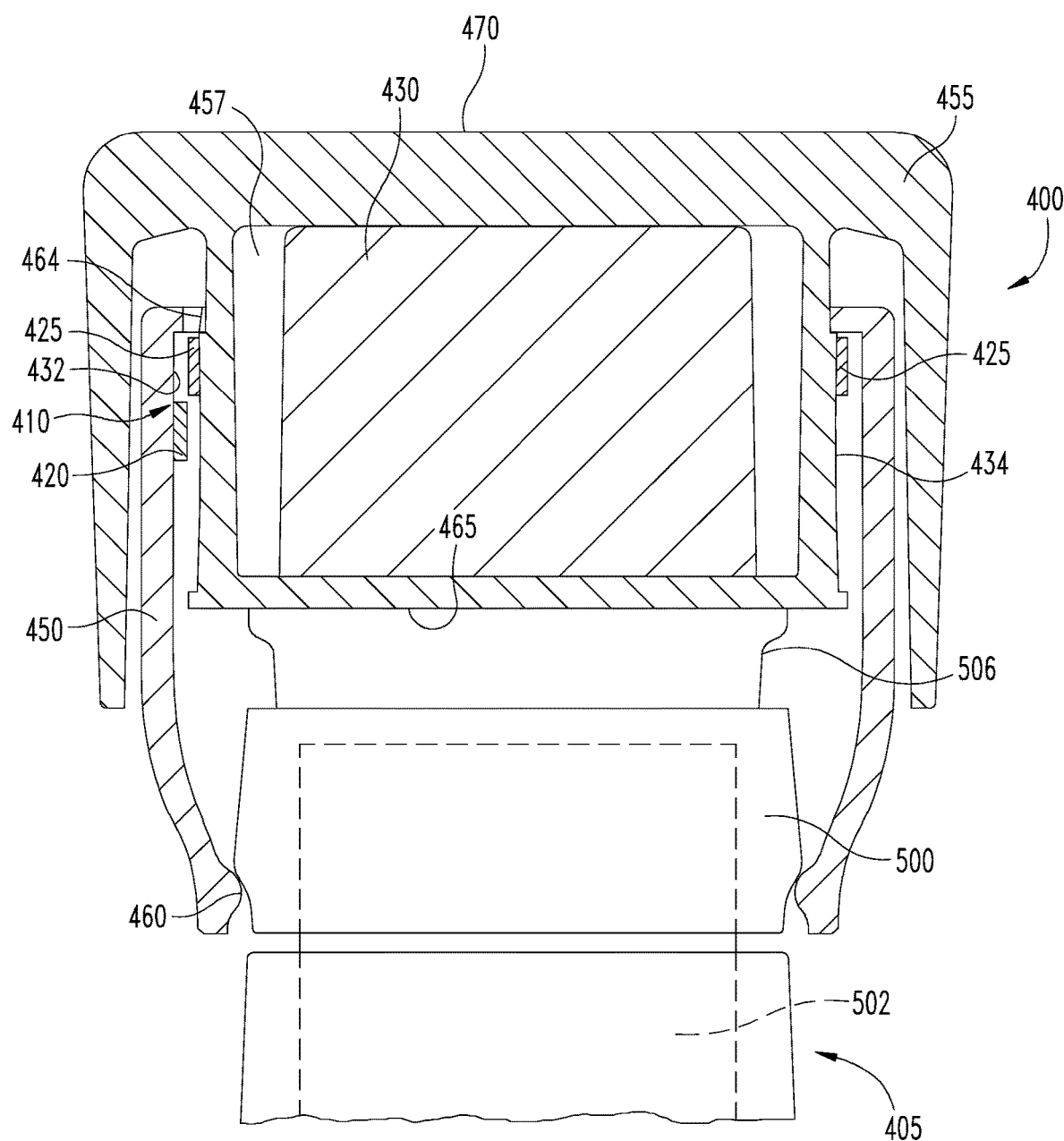
FIG. 13 is a cross-sectional view, taken along line 13-13 in FIG. 11, of the dose delivery detection module, with a portion of the remainder of the device shown not in cross-section.

With additional reference to FIG. 13, sensing system 410 includes a wiper 420 and a sensing band 425. Wiper 420 is coupled to and projects radially inwardly from an interior circumferential surface 432 of a module housing part 450. Sensing band 425 is coupled to and rings the radially outer periphery or surface 434 of module housing part 455. Sensing band 425 is shown in FIG. 13 as being axially offset slightly above the axial center of wiper 420 due to housing part 455 shifting axially downward relative to housing part 450 during dose delivery in an amount equal to the axial offset shown in FIG. 13, which figure represents the device as configured before a dose setting. During dose delivery the sensing band 425 and wiper 420 are completely radially aligned. Sensing band 425 is electrically connected with not shown wiring to controller 430 secured within an interior hollow 457 of housing part 455. Other than as described herein and the reversal of the radial positions of the components, and that such components are used for sensing a dose delivered instead of a set dose as further described below, wiper 420, sensing band 425 and controller 430 are structured and function similarly to the corresponding wiper 185, sensing band 180 and controller 170 of device 100.

Module housing part 450 includes a connection 460 complementarily shaped to a skirt 500 of the dose dial assembly 502 for a removable mounting of module 400 to the remaining portion of the delivery device 405. Skirt 500 is shown separately formed from but is fixedly secured, both rotatably and axially, with the dose dial assembly 502, and the connection 460 results in housing part 450 being rotatably and axially fixed with the dial assembly 502. Module housing part 455 includes a base face 465 that engages a top surface 504 of a button 506 to be rotatably fixed therewith.

For the device of FIGS. 11-13 to be set for delivery, module 400 is rotated relative to pen housing 508, which screws dial assembly 502 and button 506 upward and together relative to the pen housing 508. A splined connection indicated at 464 between housing parts 450 and 455 aids in keeping these housing parts rotating together during dose setting.

For the device of FIGS. 11-13 to deliver a set dose, by the user applying a plunging force on the top surface 470 of housing part 455, housing part 455, as well as button 506, are moved downward without rotation relative to housing part 450 and the dial assembly 502. This motion disconnects the splined connection 464 as well as a not shown clutch connection between button 506 and dial assembly 502, and causes an alignment of sensing band 425 with wiper 420. Further plunging moves housing part 455 and button 506 axially downward without rotation while simultaneously screwing the housing part 450 and the dial assembly 502 back into pen housing 508. The relative rotation of housing parts 450 and 455 is sensed by the operative interaction of wiper 420 with sensing band 425, which allows the controller 430 to determine the dose delivered.

Device portion 405 may be equivalent to a Humalog® KwikPen® from Eli Lilly and Company, which is taught in U.S. Pat. No. 7,291,132, the entire contents of which are incorporated herein by reference. Further details of dose delivery detection module 400 will be appreciated from U.S. Provisional Patent Application No. 62/362,808 filed Jul. 15, 2016, entitled DOSE DETECTION MODULE FOR A MEDICATION DELIVERY DEVICE, the entire contents of which are incorporated herein by reference.

Referring now to FIGS. 14-21, there is shown pertinent parts of an alternate medication delivery device with sensing system, generally designated 600. The sensing system of device 600 is configured to determine both the amount of the dose set and the amount of the dose delivered by operation of the device.

Other than for differences apparent from the following description and associated figures, device 600 can be configured the same as device 100. The description of device 600 includes further details of the configuration of its mechanical drive assembly corresponding to assembly 156 of device 100, as well as further details of the sensing system suited for mechanical drive assemblies of such type. Reference to parts that are the same as in device 100 use the same reference numbers as used with device 100 to facilitate explanation.

Figure 14:
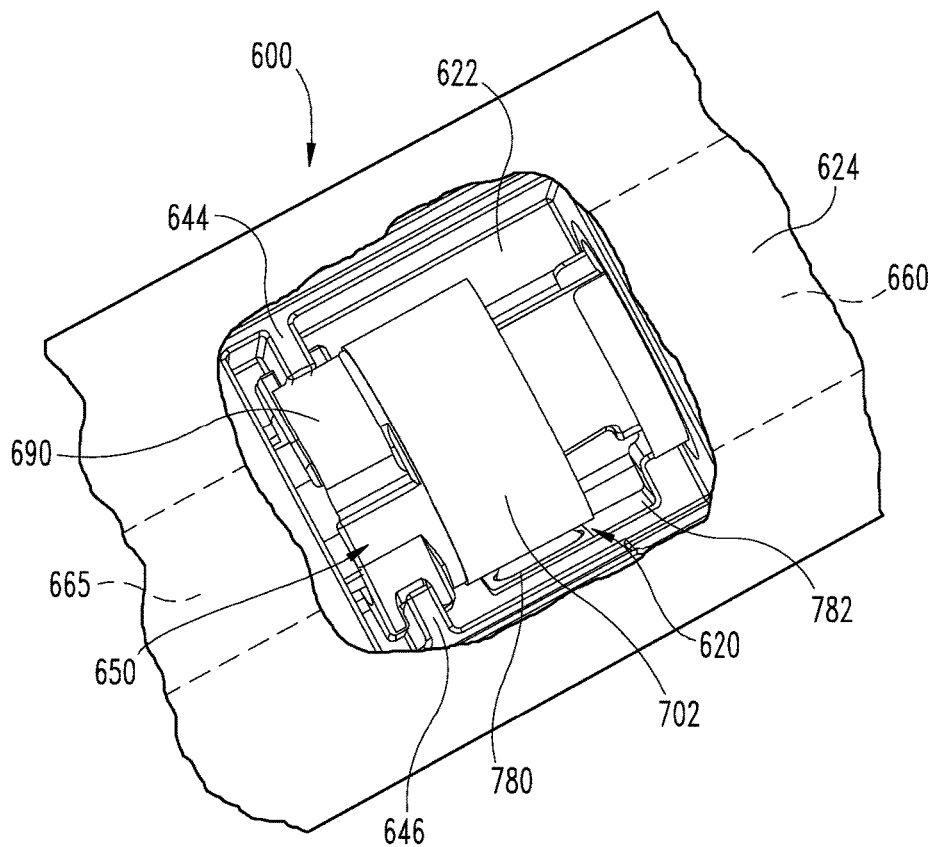
FIG. 14 is a partial perspective view, and with a region removed to reveal the interior, of an alternate embodiment of a medication delivery device with sensing system.

With reference initially to FIG. 14, the device sensing system, generally designated 620, is visible within a housing compartment 622 due to a portion of the exterior main housing 624 having been removed. Housing compartment 622 is shaped to receive the sensing system 620 and includes alignment ribs 644 and 646 that project radially inward to support core member 650 and maintain it rotationally and axially fixed relative to the housing 624.

Sensing system 620 is coupled to select members of device 600 which are relatively rotatable in proportion to the amount of the set dose, and which are relatively rotatable in proportion to the amount of the injected or delivered dose. These members include barrel 660, drive sleeve 665 and core member 650.

Figure 15:
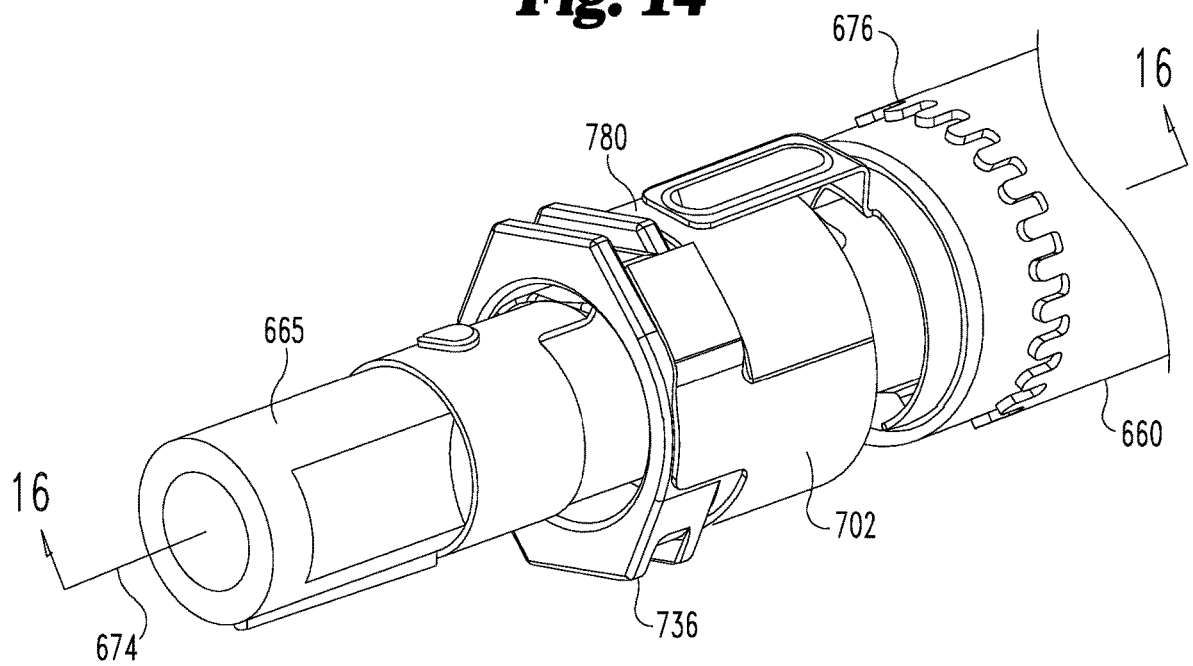
FIG. 15 is a partial perspective view of select portions of the device with sensing system of FIG. 14.
Figure 16:
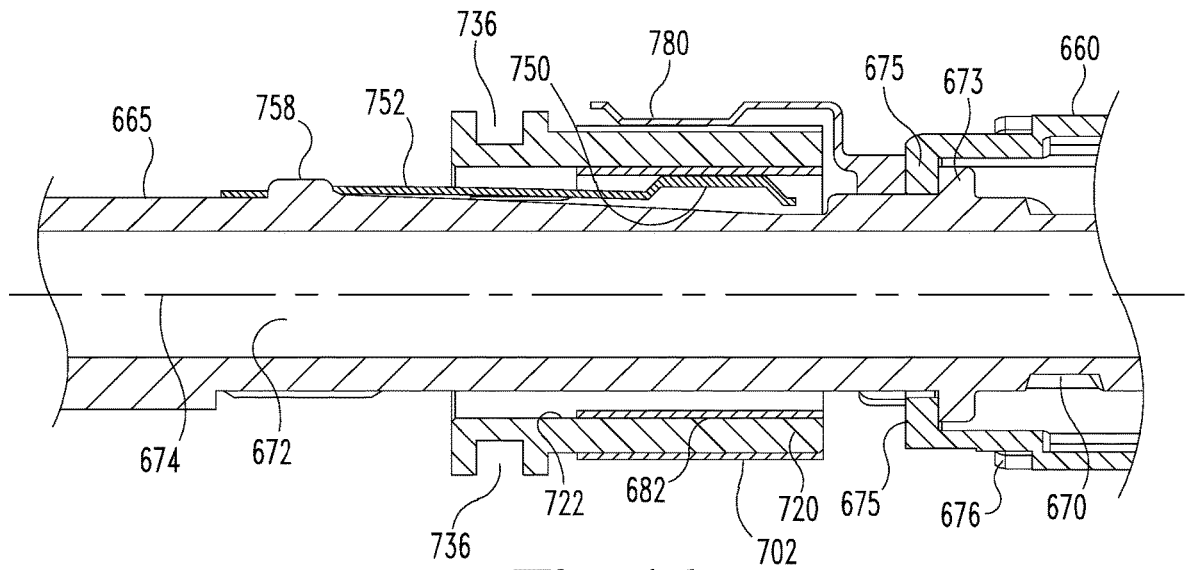
FIG. 16 is a longitudinal cross-sectional view taken along line 16-16 of FIG. 15.

With additional reference to FIGS. 15 and 16, barrel 660 is a sleeve that is keyed to rotate with, but be axially movable relative to, tube 154. The drive sleeve 665 includes external threading 670 that is engaged by internal threading of tube 154. An internal axial hollow 672 of drive sleeve 665 receives threaded shaft 165 therein. A not shown keying between drive sleeve 665 and threaded shaft 165 means that a rotation of drive sleeve 665 within housing compartment 622 causes a corresponding rotation of shaft 165 which advances that shaft axially to eject medication from the device 600.

During dose setting, as knob 152 and tube 154 are turned to screw out axially together from the device housing, barrel 660 rotates within the housing 624 about axis of rotation 674 while drive sleeve 665 does not rotate about axis of rotation 674 due to a not shown spline connection between the device housing 624 and drive sleeve 665.

When dose knob 152 is plunged by a user to deliver a dose, that plunging initially produces a transitioning translational movement of drive sleeve 665, due to an axial force transmitted by tube 154 at the external threading 670, which due to an axial force transmitted by sleeve flange 673 to barrel shoulder 675 causes a transitioning translational movement of barrel 660. This transitioning movement does not cause tube 154 and barrel 660 to rotate because a torque required to overcome a spring-biased, housing-engaging dose clicker (not shown) splined to barrel 660 is greater than the torque generated at the threading 670. This translational movement, occurring against a resistive axial force provided by the not shown clicker spring, moves splines 676 of barrel 660 axially into engagement with not shown complementary housing splines while releasing the not shown spline connection between the device housing and drive sleeve 665. Further user plunging of dose knob 152 causes drive sleeve 665 and thereby shaft 165 to rotate about axis of rotation 674, causing medicament to be ejected, while barrel 660 does not rotate about axis of rotation 674 due to its splined connection with the housing.

Figure 17:
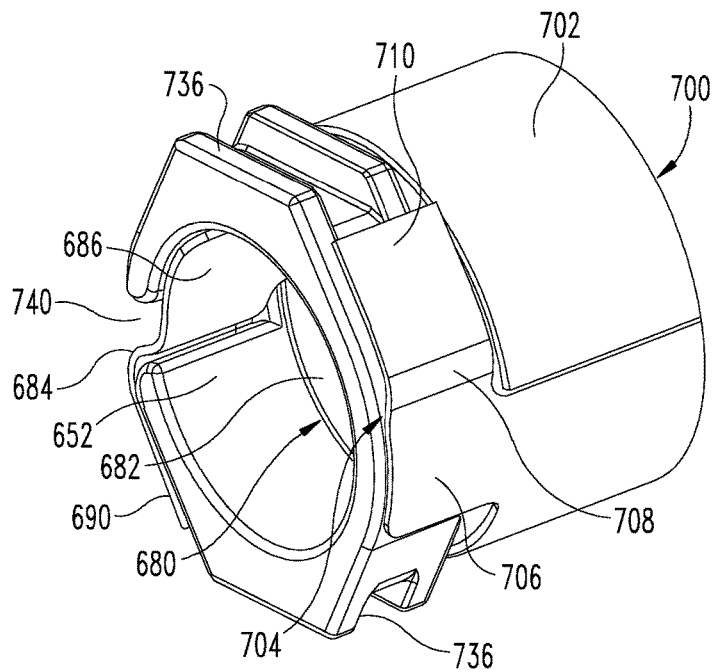
FIG. 17 is a perspective view similar to FIG. 15 showing only the sensing bands and the core member.
Figure 18:
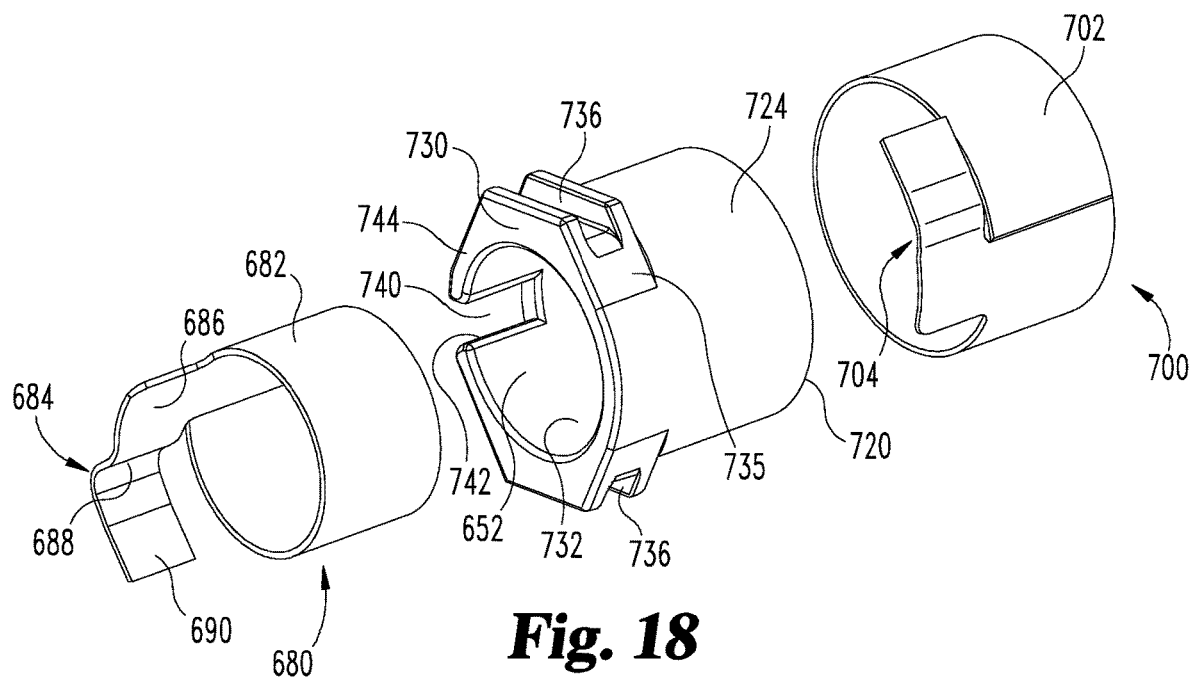
FIG. 18 is an exploded perspective view of the components shown in FIG. 17.

With additional reference to FIGS. 17 and 18, sensing system 620 includes sensing bands 680 and 700. Sensing band 680 includes a wiper sensing portion 682 formed in a cylindrical sleeve shape, and a connector leg 684. The sensing portion 682 is a single assembled unit including two angularly staggered pairs of conductor-resistor strips extending circumferentially within the sleeve similarly to that described above for sensing bands 180a and 180b. Alternatively sensing portion 682 can be constructed similarly to sensing band 180. Connector leg 684 contains the electrical leads circuited with the associated two conductor-resistor strip pairs. Connector leg 684 includes a first region 686 that extends directly from the sensing portion 682 in an axial direction. A transition region 688 extends in the angular direction from first region 686 and terminates in an end region 690 that includes not shown electrical connections that can be a printed extension of lead end 228 and can be circuited with the electrical leads, such as a ZIF (Zero Insertion Force) connector, that are circuited with the conductor-resistor strip pairs of sensing portion 682. The electrical connections are provided on the outer radial periphery of end region 690 for electrical connection during assembly with circuitry routed to the controller of device 600. First region 686 is arranged in the same curved plane as sensing portion 682, while transition region 688 juts outward from first region 686 in the radial direction. End region 690 extends from transition region 688 to lay over the core member exterior to enable electrical connection to the rest of the circuitry with the ability to transition into a flat connection.

Sensing band 700 includes a wiper sensing portion 702 formed in a cylindrical sleeve shape, and a connector leg 704. Wiper sensing portion 702 has a larger diameter than wiper sensing portion 682 to fit around it. Sensing band 700 is a single assembled unit including two angularly staggered pairs of conductor-resistor strips extending circumferentially within the sleeve similarly to that described above for sensing bands 180a and 180b, but typically with the conductor strips located radially outward of their respective resistor strips. Alternatively, sensing portion 702 can be constructed similarly to sensing band 180, with the resistor and conductor strips typically reversed. Connector leg 704 contains the electrical leads circuited with the associated two conductor-resistor strip pairs. Connector leg 704 includes a first region 706 that extends directly from the sensing portion 702 in an axial direction and in the same curved plane as sensing portion 702. A transition region 708 extends in the angular direction from first region 706 with an offset to extend outward radially to allow a service loop to aide in connection of 710 to other circuitry. End region 710 of connector leg 704 extends in a curved shape from transition region 708 to lay over the core member exterior and includes not shown electrical connections, as previously described in relation to end region 690, on its outer radial periphery circuited with the electrical leads within the connector leg 704 and for electrical connection during assembly with circuitry routed to the controller of device 600.

Core member 650 is formed in one-piece of a rigid plastic and includes an interior bore or hollow therethrough 652. Core member 650 has a sleeve portion 720 with a cylindrical, radially inner periphery or surface 722 and a cylindrical, radially outer periphery or surface 724. Core member 650 includes keyed portion 730 at the distal end of sleeve portion 720. Keyed portion includes a cylindrical, radially inner surface 732 that is an axial continuation of sleeve portion surface 722. The radially outer surface 735 has channeled sections 736 that fit over alignment ribs 644 and 646 to provide alignment for installation within the housing compartment 622 and to prevent core member 650 from rotating or shifting axially within housing 624 during use. While core member 650 is shown as a single piece that is effectively connected to the housing, such a design is not necessary but facilitates manufacture and assembly. In alternate embodiments, a core member can be integrally formed with the outer housing, or formed of multiple parts assembled together and then installed to the housing.

Sensing bands 680 and 700 are each mounted to core member 650 to be rotationally and axially fixed with core member 650, and therefore indirectly axially and rotationally fixed with housing 624. Such mounting can be with adhesives, or an alternate manner such as mechanical fasteners or a friction fit.

Sensing band 680 is arranged such that wiper sensing portion 682 wraps along or layers the full circumference of the cylindrical radially inner surface 722, connector leg first region 686 extends along cylindrical radially inner surface 732, transition region 688 fits through a slot-shaped opening 740 provided through keyed portion 730 by a notch 742 in its distal end 744, and end region 690 overlays radially outer surface 735.

Sensing band 700 is arranged such that wiper sensing portion 702 is radially aligned with and radially outward of wiper sensing portion 682 and directly sandwiching core sleeve portion 720 therebetween such that the two sensing layers provided by sensing bands 680 and 700 are separated only by core sleeve portion 720. Wiper sensing portion 702 wraps along the full circumference of the cylindrical radially outer surface 724, with connector leg first region 706, transition region 708 and end region 710 overlaying radially outer surface 735 of keyed portion 730.

A wiper element 750 coupled to drive sleeve 665 that extends through core bore 652 is positioned radially inward of and slidingly engages wiper sensing portion 682. Wiper element 750 is rigid and has a suitable axial length to effectively engage the wiper sensing portion 682 at all times of device operation. Such a design allows the drive sleeve rotational position to be checked even when it should not be rotating during a dose setting. Wiper element 750 projects radially outward from a stepped arm 752 that extends axially from a C-shaped clip or mount 754. A cut-out or depression 675 in the periphery of drive sleeve 665 underneath the wiper element 750 and arm 752 serves as clearance for arm 752 to flex.

Figure 19:
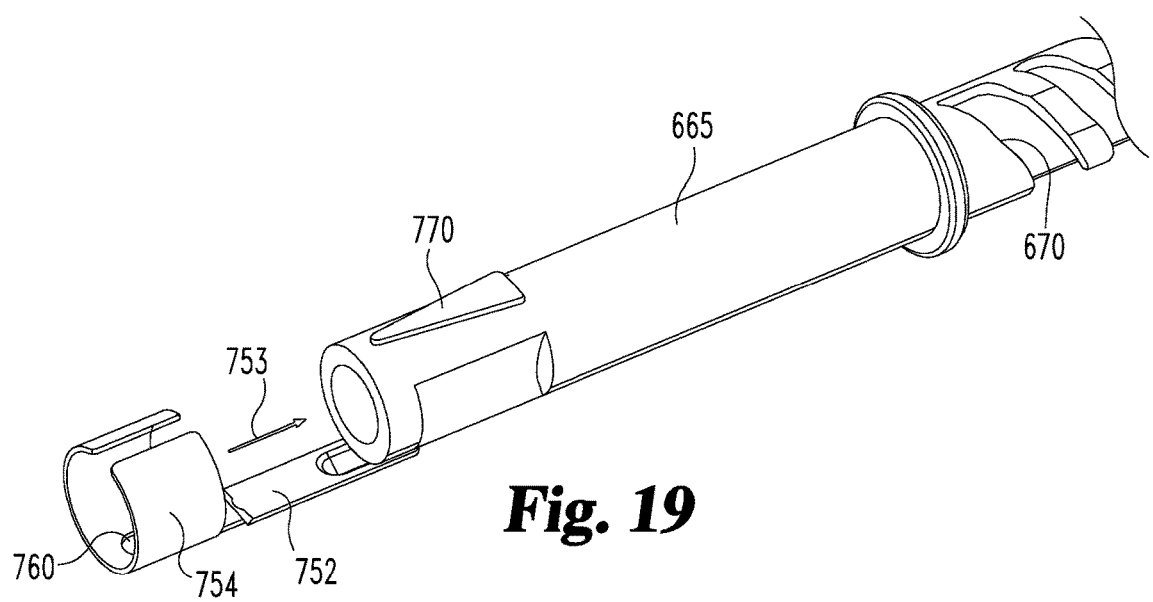
FIG. 19 is a partial, exploded perspective view of a wiper component and drive sleeve of the medication delivery device with sensing system of FIG. 14.
Figure 21:
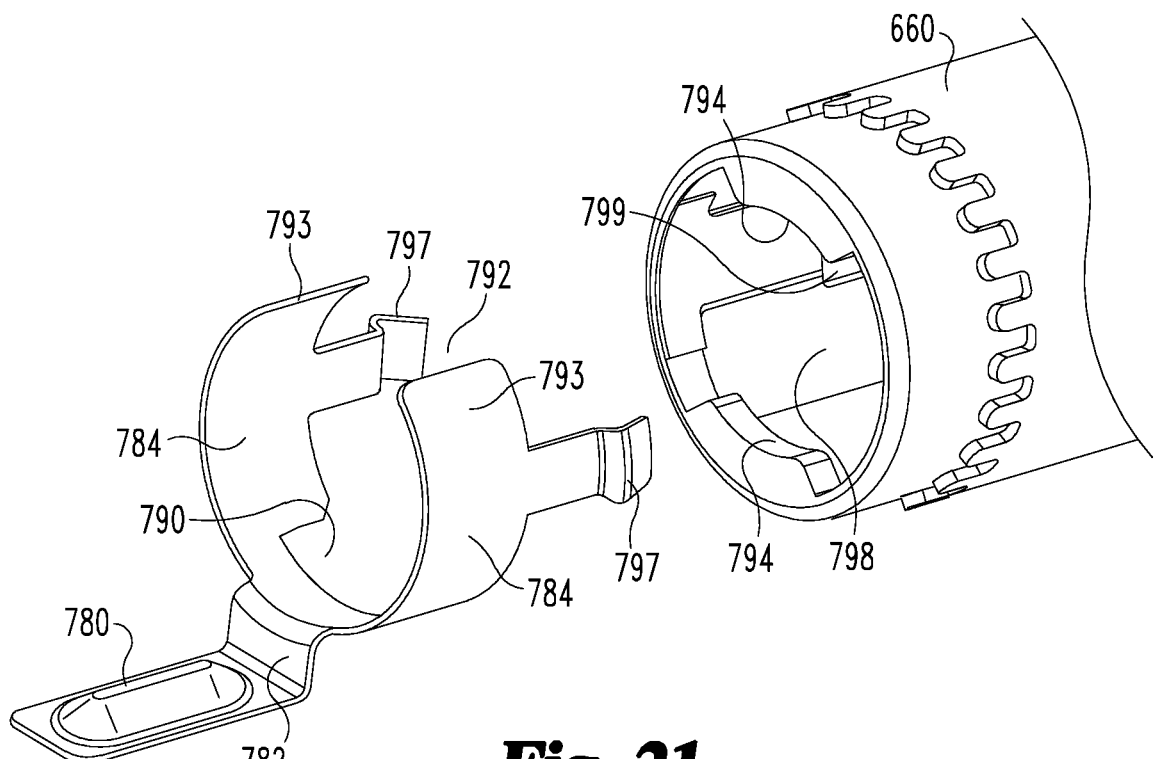
FIG. 21 is a partial and exploded perspective view of a wiper component and barrel of the medication delivery device with sensing system of FIG. 14.
Figure 20:
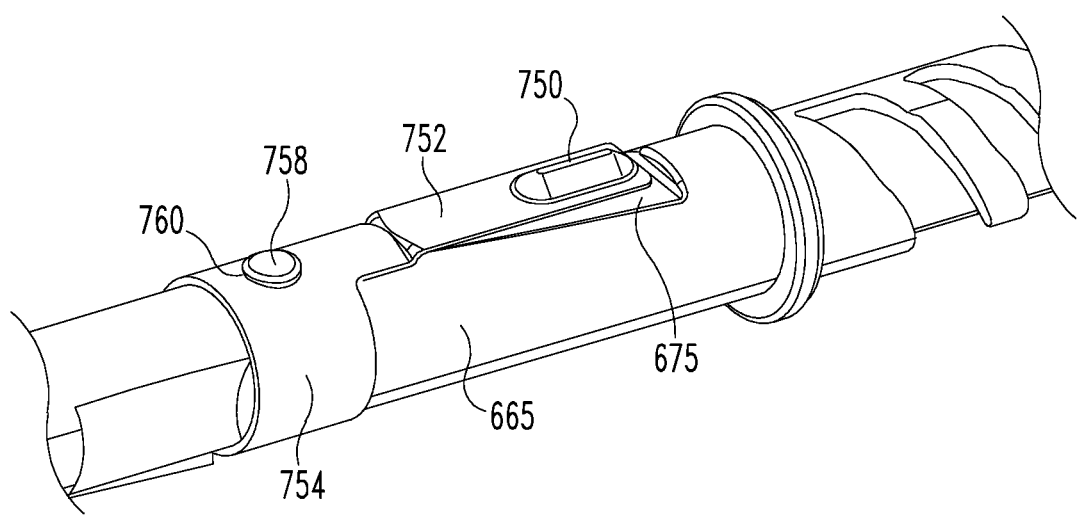
FIG. 20 is a partial, opposite perspective view of the wiper component and drive sleeve of FIG. 19.
Figure 22:
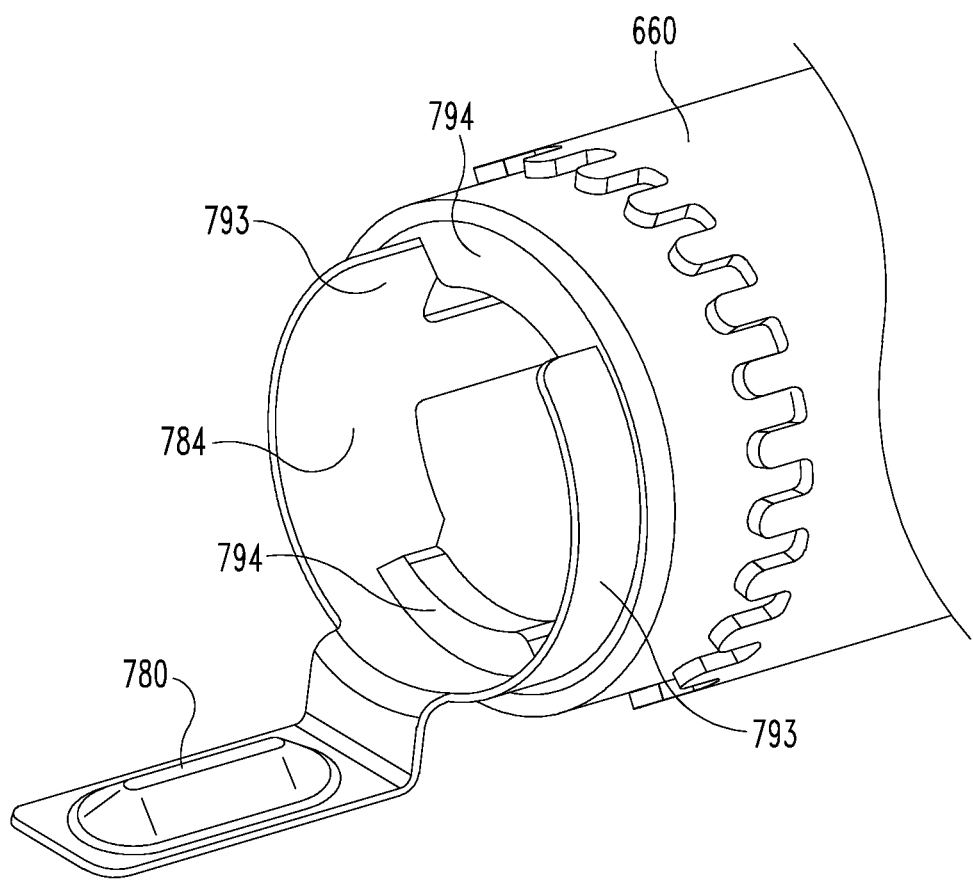
FIG. 22 is a partial perspective view of the wiper component and barrel of FIG. 21.

Wiper element 750, arm 752 and clip 754 are shown integrally formed, but can be separately formed and assembled. The material of the arm 752 and clip 754 can be a pressed stainless steel that affords sufficient resiliency for a flexing of arm 752, which flexing provides a spring loaded engagement of wiper element 750 with sensing band 680 as well as accounts for non-concentricity, and for attachment of clip 754 to drive sleeve 665. Wiper clip 754, and therefore arm 752 and wiper element 750, are rotationally and axially fixed to drive sleeve 665 via a projection 758 of drive sleeve 665 that closely fits within a complementary hole 760 in clip 754, with the resiliency of the C-shaped clip 754 gripping around the drive sleeve 665 radially periphery. As shown in FIG. 19, during manufacturing assembly of clip 754 to drive sleeve 665, as clip 754 is axially slid onto drive sleeve 665 as shown at arrow 753, clip 754 is resiliently splayed open by wedge feature 770, allowing clip 754 to be moved axially so that hole 760 fits above and then onto projection 758, at which axial position clip 754 has passed wedge feature 770 so as to snap back around the drive sleeve 665 to secure the clip as shown in FIG. 20.

A wiper element 780 coupled to barrel 660 is positioned radially outward of and slidingly engages wiper sensing portion 702. As shown in FIG. 16, the wiper element 780 can extend in an axially different direction than the wiper element 750. As shown in FIG. 16, the wiper element 780 can radially overlap the wiper element 750, being separated by the sidewall of the sleeve portion 720 of the core member 650. Wiper element 780 is positioned radially outward from wiper element 750. Wiper element 780 is rigid and has a suitable axial length to effectively engage sensing band 700 at all times of device operation. Such a design allows the barrel rotational position to be checked even when it should not be rotating during a dose injection. Wiper element 780 projects radially inward from a stepped arm 782 that extends axially from a C-shaped clip 784. Wiper element 780, arm 782 and clip 784 are shown integrally formed, such as from pressed stainless steel, but can be separately formed and assembled. Arm 782 is flexible and provides a spring loaded engagement of wiper element 780 with sensing band 700 and to account for non-concentricity.

Wiper clip 784, and therefore arm 782 and wiper element 780, are rotationally fixed to barrel 660 by a keyed connection using a notch 790 in clip 784 and a space 792 between the ends 793 of the two clip legs to closely receive two tangs 794 that project inward within the hollow 798 of barrel 660. Wiper clip 784, and therefore arm 782 and wiper element 780, are shown axially fixed to barrel 660 by axially extending, detented springs 797 that snap fit into indents 799 on the barrel interior surface, but can be alternatively secured such as using adhesive or mechanical fasteners, such as radial crimps.

As will be appreciated from an understanding of the operation of device 600 described above, the relationship of wiper element 780 with sensing band 700 allows a rotation of the barrel 660 relative to the core member 650 and housing 624 to be sensed to allow a dose set for device 600 to be identified by a controller, and the relationship of wiper element 750 with sensing band 680 allows a rotation of the drive sleeve 665 relative to the core member 650 and housing 624 to be sensed to allow a dose delivered for device 600 to be identified by the controller.

Figure 23:
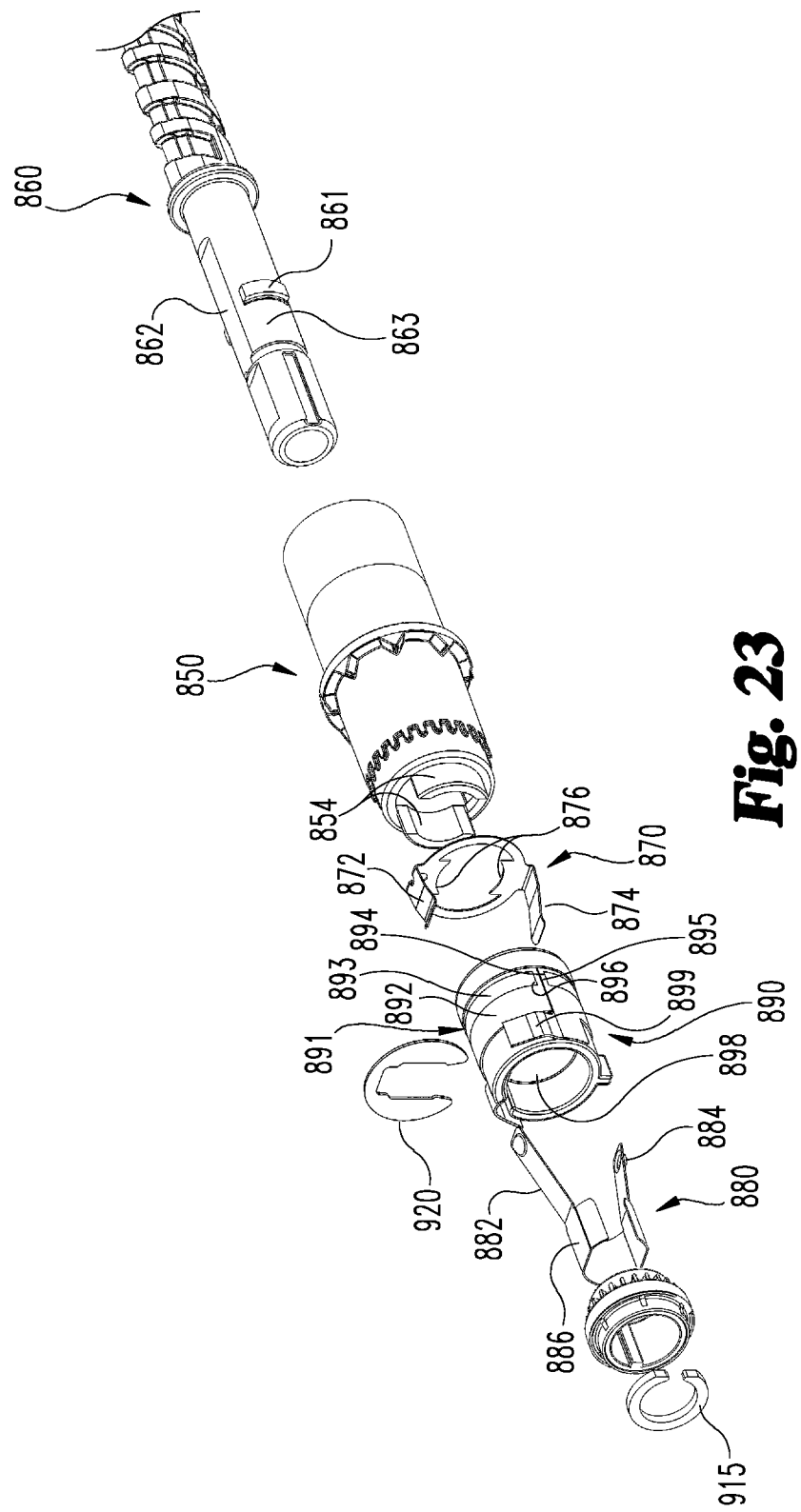
FIG. 23 is a perspective view, in partially exploded form, of portions of an alternate embodiment of a medication delivery device with sensing system.
Figure 24:
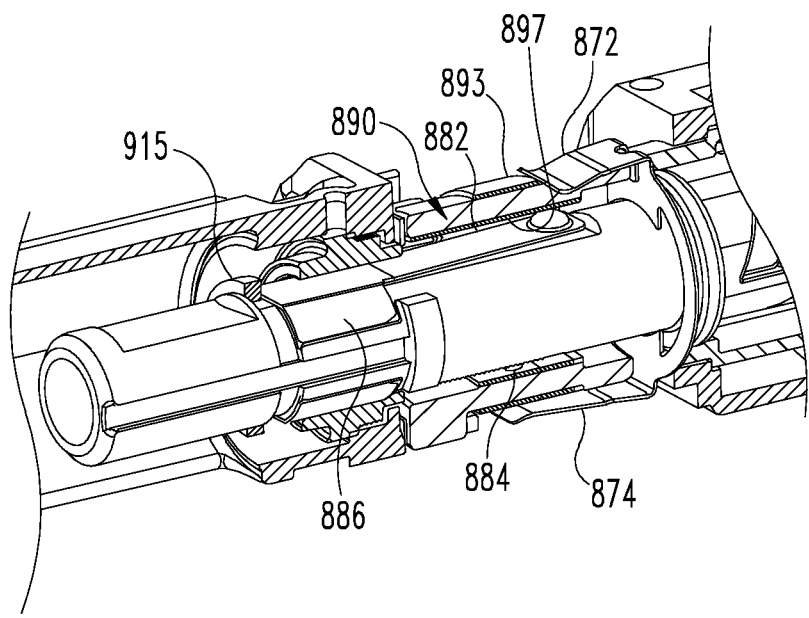
FIG. 24 is a partial perspective view, partially in longitudinal cross-section, of the device portions of FIG. 23 within a housing piece.
Figure 25:
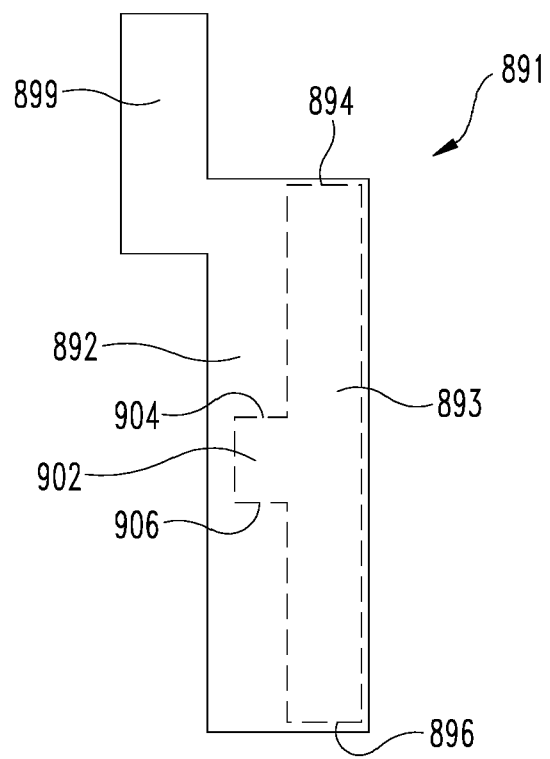
FIG. 25 is an abstract view of a sensing band of the sensing system from FIG. 23 in an uncurved, or straight, configuration.

Referring now to FIGS. 23-25, there is shown pertinent parts of an alternate medication delivery device with sensing system. As with the device 600, the device of FIGS. 23-25 also is configured to determine both the amount of the dose set and the amount of the dose delivered by operation of the device. The device of FIGS. 23-25 uses a modified sensing band having different regions of common electrical strips cooperating with a pair of wiper elements. It will be appreciated that the device of FIGS. 23-25 can be similar in overall operation to device 600.

The device includes a barrel 850, a drive sleeve 860 that transmits its rotation, via a not shown mechanical drive train, to a not shown threaded shaft used to eject medication, and a core member 890 that is rotationally fixed to the device housing and axially unconstrained to the device housing such that it can slide axially relative to the device housing.

A wiper assembly, generally referenced at 880, is fixedly coupled to drive sleeve 860 to rotate and move axially therewith, and to extend within bore 898 of core member 890. Wiper assembly 880 includes a pair of wipers 882 and 884, each formed of a wiper element on a flexible arm. The wiper elements of wipers 882 and 884 are shown as outwardly facing, convex surfaces projecting from the arms, but need not be so shaped or projecting. Wipers 882 and 884 extend axially from and are integrally formed with a C-shaped clip or mount 886 at locations 180 degrees apart from each other. Wiper 882 extends further axially from mount 886 than does wiper 884 as further described below. Wiper 882 can flex within depression 862 of drive sleeve 860 while wiper 884 similarly can flex within a depression on the side of drive sleeve 860 opposite depression 862. Wiper mount 886 secures around axial portion 863 of drive sleeve 860 so that wiper assembly 880 rotates with the drive sleeve, and wiper assembly 880 does not move axially relative to drive sleeve 860, such as due to the axial capture of wiper mount 886 via a shoulder 861 formed on drive sleeve 860 and frictional interaction on the internal face of wiper mount 886.

A wiper assembly, generally referenced at 870, is fixedly coupled in a suitable fashion to barrel 850 so as to rotate and move axially therewith. Wiper assembly 870 includes a pair of wipers 872 and 874, each formed of a wiper element on a flexible arm. The wiper elements of wipers 872 and 874 are shown as strip-engaging surfaces of their respective wiper arms, but can project from such arms. Wipers 872 and 874 extend from and are integrally formed with a wiper ring, which ring is shown as having keys 876 that closely fit within angular spaces between the opposite angular ends of arc-shaped extensions 854 of barrel 850. Wipers 872 and 874 are circumferentially disposed relative to one another substantially 180 degrees (that is, in a range of 180 degrees plus/minus 10 degrees). In one example, wipers 872 and 874 extend axially at locations 180 degrees apart from each other. Wiper 874 extends further axially forward than does wiper 872 (that is, axially offset from one another) as further described below.

Core member 890 is constrained to move axially with drive sleeve 860 and barrel 850 when drive sleeve 860 and barrel 850 move together axially within the device housing during mode transitioning of the device. In the shown embodiment, core member 890 is driven forward within the device housing by a thrust face of wiper assembly 870 when the device transitions from dial mode to injection mode. Clip 920 is an axial thrust washer/clip that locks onto the drive sleeve 860 and is used to pull core member 890 back within the device housing when the device returns to dial mode after being in injection mode.

Each of wiper assemblies 870 and 880 cooperates with a different sensing band, each of which sensing bands has a single pair of particularly shaped conductor-resistor strips extending therein that are shaped to have different regions be engaged by the wiper elements of the wiper assemblies. In particular, wiper assembly 870 cooperates or functions with a sensing band, generally designated 891, that wraps around the exterior of core member 890. Wiper assembly 880 cooperates with a sensing band shown in cross section in FIG. 24 and generally referenced 897 which wraps the interior of core member 890. Each sensing band 891 and 897 is rotationally and axially fixed with core member 890 and therefore indirectly rotationally fixed to the device housing. The sensing bands 891 and 897 are mounted on the core member 890 similarly to the manner that sensing bands 680 and 700 fit within, around and through core member 650.

With additional reference to the flattened configuration of the sensing band shown in FIG. 25, the construction and design of sensing band 891 will be further explained. This explanation of sensing band 891 also applies to sensing band 897 which is similarly configured, though sensing band 891 works with wiper assembly 870 to sense barrel position while sensing band 897 works with wiper assembly 880 to sense drive sleeve position. Sensing band 891 is shown including a sensing portion 892 that holds the sensing strip pair and which when installed is in a cylindrical sleeve shape. Connector leg 899 is used for making an electrical connection between the sensing strip pair within sensing portion 892 and the device controller.

The effective shape of the pair of conductor-resistor strips extending within sensing portion 892, and thereby the effective sensing area of sensing portion 892, is shown in FIG. 25 in dashed lines. The sensing area includes a main path 893 and a secondary path 902 that are different regions of the same electrical strips so as to be electrically integrated, thereby allowing the controller to receive a single electrical output from the sensing band 891 whether produced by the main path 893 or the secondary path 902. Main path 893 continuously extends between angular ends 894 and 896. Main path 893 is axially positioned within the device to be axially operatively aligned for contact with the wiper element of wiper 872. Main path 893 is never contacted by wiper 874 as barrel 850 is rotated during use. When sensing band 891 is installed around core member 890, the main path 893 almost completely rings the core member periphery. The only periphery portion not ringed is a small angular region or gap 895 of that periphery between the facing angular ends 894 and 896. The device controller is able to determine where along the angular length of main path 893 the wiper element of wiper 872 operatively contacts the main path 893, allowing a position of the barrel 860 relative to the core member 890 to be sensed to allow a dose set for the device to be identified by the controller.

Secondary path 902 continuously extends between angular ends 904 and 906 and juts directly from main path 893 in the axially forward direction. Secondary path 902 is axially positioned within the device to be axially operatively aligned for contact with the wiper element of wiper 874, and is never contacted by wiper 872. Secondary path 902 has an angular length extending between ends 904 and 906 which covers the length of the angular gap 895. Secondary path 902 is positioned along the angular length of main path 893 in view of the angular spacing between the wiper elements of wipers 872 and 874 so as to realize a design in which wiper 874 engages secondary path 902 at all times wiper 874 is within angular gap 895 and not operatively contacting main path 893. Secondary path 902 is shown positioned halfway along the angular length of main path 893 due to wipers 872 and 874 begin spaced 180 degrees apart around the core member 890, but in alternate embodiments can be positioned differently to account for different angular spacings of the wipers. Alternatively, the secondary path 902 may be formed as a separate second sensing band (not shown) axially disposed adjacent to the main path 893 of the first sensing band. The separate second sensing band is contactedly associated with the wiper 874, while the first sensing band with main path 832 is contactedly associated with the wiper 872.

The device controller recognizes barrel rotational position from the single electrical signal it receives from sensing band 891. During the majority of barrel rotation, the magnitude of the electrical signal to the device controller reflects where the wiper 872 engages main path 893, during which time wiper 874 is not engaged with secondary path 902. When wiper 872 enters the rotary gap 895 to no longer engage main path 893, the wiper 874 simultaneously engages secondary path 902 to short the signal to the controller notably differently from where the signal was being shorted by wiper element 872 immediately prior. This changed signal value, as well as the value of that signal as it further changes as the wiper 874 moves along the angularly length of secondary path 902, allows the controller to recognize barrel rotational position until the wiper 872 again engages main path 893 while the wiper 874 moves off secondary path 902.

It will be appreciated that rather than being the same angular length as gap 895, secondary path 902 can have an angular length longer, such as a few degrees longer, than the angular length of gap 895. In such a design, while there would always be at least one wiper in contact with the sensing band for all possible rotational or angular positions of the relevant sensed member, there also will be certain rotational positions of the sensed member for which wiper 874 engages the few degrees longers section of the secondary path 902 while wiper 872 also engages main path 893. At such certain rotational positions, it is appreciated that the single signal that sensing band 891 sends to the device controller, depending on the electrical configuration of the sensor, can introduce uncertainty for the controller, such as the output signal being generated by sensing band 891 being an averaging of the signals otherwise sent by wipers 874 and 872 contacting their respective paths. This uncertainty can be resolved in the device by an initialization action involving active rotation of the wiper over a sufficiently large angular distance as to provide the controller with a continuous characteristic signal from sensing band 891 to enable the controller to resolve a known reference position.

While this invention has been shown and described as having preferred designs, the present invention can be modified within the spirit and scope of this disclosure. For example, module 400 can sense dose setting amounts if adapted to work with a device portion having suitable parts that experience relative rotation during dose setting. This application is therefore intended to cover any variations, uses or adaptations of the invention using its general principles. Further, this application is intended to cover such departures from the present disclosure as come within known or customary practice in the art to which this invention pertains.

While the invention has been illustrated and described in detail in the drawings and foregoing description, the same is to be considered as illustrative and not restrictive in character. All changes, equivalents, and modifications that come within the spirit of the inventions defined by the claims included herein are desired to be protected.

Various aspects are described in this disclosure, which include, but are not limited to, the following aspects:

1. A medication delivery device including: a first member and a second member rotatable relative to the first member about an axis of rotation in proportion to at least one of an amount of a dose set and an amount of a dose delivered by operation of the medication delivery device; a radially projected wiper coupled to the first member; an electrically operable sensing band coupled to the second member, the sensing band arranged in a curved shape and radially disposed relative to and in contacting relationship with the wiper, wherein, during relative rotation between the first and second members, the sensing band is operable to generate outputs associated with the relative angular position of the wiper along an operational angular length of the sensing band that is indicative of relative rotational positions of the first and second members; and a controller electrically coupled with the sensing band to determine, based on the outputs generated by the sensing band, at least one of the amount of the dose set and the amount of the dose delivered by operation of the medication delivery device.

2. The medication delivery device of aspect 1, further including a radially projected second wiper coupled to the first member, and an electrically operable second sensing band coupled to the second member, the second sensing band arranged in a curved shape and radially disposed relative to and in a contacting relationship with the second wiper, wherein the second sensing band is disposed axially relative to the sensing band, wherein, during relative rotation between the first and second members, the second sensing band is operable to generate outputs associated with the relative angular position of the second wiper along an operational angular length of the second sensing band that is indicative of relative rotational positions of the first and second members, wherein the controller is electrically coupled with the second sensing band to determine, based on the outputs generated by the second sensing band, at least one of the amount of the dose set and the amount of the dose delivered by operation of the medication delivery device.

3. The medication delivery device of aspect 2, where the second wiper extends axially further than the first wiper.

4. The medication delivery device of aspect 4, where the sensing band configured to accommodate the first and second wipers.

5. The medication delivery device of any one of aspects 2-4, where the second wiper is circumferentially disposed relative to the first wiper by substantially 180 degrees.

6. A medication delivery device including: a first member and a second member rotatable relative to the first member about an axis of rotation in proportion to an amount of a dose set by operation of the medication delivery device; a third member and a fourth member rotatable relative to the third member about the axis of rotation in proportion to an amount of a dose delivered by operation of the medication delivery device; a first wiper coupled to the first member and projecting in a radial direction; a second wiper coupled to the third member and projecting in a radial direction; an electrically operable first sensing band coupled to the second member; an electrically operable second sensing band coupled to the fourth member, each of the first and second sensing bands arranged in a curved shape and radially disposed relative to and in a contacting relationship with the first and second wipers, respectively, wherein, during relative rotation between the first and second members and relative rotation between the third and fourth members, each of the first and second sensing bands is operable to generate outputs associated with the relative angular position of the corresponding first and second wipers along an operational angular length of the respective first and second sensing bands that is indicative of relative rotational positions of the first and second members and the third and fourth members; and a controller electrically coupled with each of the first and second sensing bands to determine, based on the outputs generated by the first and second sensing bands, the amount of the dose set and the amount of the dose delivered by operation of the medication delivery device.

7. The medication delivery device of aspect 6, wherein the second member and the fourth member are integrally formed as a single core member.

8. The medication delivery device of any one of aspects 6-7, further including a pair of first wipers coupled to the first member and a pair of second wipers coupled to the third member.

9. The medication delivery device of aspect 8, further including a pair of electrically operable first sensing bands coupled to the second member and associated with the pair of first wipers; and a pair of electrically operable second sensing bands coupled to the fourth member and associated with the pair of second wipers.

10. A medication delivery device including: a first member of the medication delivery device; a second member of the medication delivery device rotatable relative to the first member in proportion to at least one of an amount of a dose set and an amount of a dose delivered by operation of the medication delivery device, the first and second members relatively rotatable about an axis of rotation extending in an axial direction; a sensing system operable to detect relative rotational positions of the first and second members and generate outputs correlated to such relative rotational positions, the sensing system including: a wiper rotationally coupled to the first member and projecting in a radial direction; a sensing band rotationally coupled to the second member and circuited with an electrical power source, the sensing band arranged in a curved shape around the axis of rotation and having an operational angular length, the sensing band disposed in the radial direction inward or outward of the wiper for a physical contact with the wiper as the second member rotates relative to the first member, the sensing band having an electrical characteristic correlated with where along the operational angular length of the sensing band is operationally engaged in the radial direction due to the physical contact with the wiper; and a controller electrically circuited with the sensing system to identify, based on outputs of the sensing system, at least one of the amount of the dose set and the amount of the dose delivered by operation of the medication delivery device.

11. The medication delivery device of aspect 10, wherein at least one of the wiper and the sensing band is radially resilient to assist the maintenance of the wiper and the sensing band in physical contact as the second member rotates relative to the first member.

12. The medication delivery device of any one of aspects 10-11, wherein at least one of the wiper and the sensing band is radially biased relative to the first and second members to which each is respectively rotationally coupled to assist the maintenance of the wiper and the sensing band in physical contact as the second member rotates relative to the first member.

13. The medication delivery device of any one of aspects 10-12, wherein the sensing band is disposed radially outward of the wiper.

14. The medication delivery device of any one of aspects 10-13, wherein the second member comprises a housing of the medication delivery device.

15. The medication delivery device of aspect 14, wherein the sensing band is attached directly to an interior circumferential surface of the housing.

16. The medication delivery device of aspect 14, wherein the sensing band is disposed on a component that is at least rotatably fixedly mounted to the housing.

17. The medication delivery device of any one of aspects 10-16, wherein the operational angular length extends only partially around a circumference of the second member.

18. The medication delivery device of aspect 17, wherein the operational angular length extends at least 345 degrees but less than 360 degrees around an inner circumference of the second member.

19. The medication delivery device of any one of aspects 10-18, wherein the sensing system comprises a second wiper rotationally coupled to the first member and projecting in the radial direction, and a second sensing band rotationally coupled to the second member and the electrical power source, the second sensing band arranged in a curved shape around the axis of rotation and having an operational angular length, the second sensing band disposed in the radial direction inward or outward of the second wiper for a physical contact with the second wiper as the second member rotates relative to the first member, the second sensing band having an electrical characteristic correlated with where along the operational angular length of the second sensing band is engaged in the radial direction due to the physical contact with the second wiper.

20. The medication delivery device of aspect 19, wherein the operational angular lengths of the sensing band and the second sensing band are axially spaced and each only partially extends around a circumference of the second member.

21. The medication delivery device of aspect 20, wherein the wiper and the second wiper comprise different regions of a single wiper body.

22. The medication delivery device of any one of aspects 10-21, wherein the sensing system and the controller are parts of a reusable dose delivery detection module, the reusable dose delivery detection module removable from the first member and the second member for subsequent mounting to corresponding members of another medication delivery device for use therewith.

23. The medication delivery device of any one of aspects 10-22, wherein the sensing band is disposed radially outward of the wiper, the first electrical strip including a resistor strip and the second electrical strip including a conductor strip, the conductor strip disposed radially inward of the resistor strip and bendable radially outward into electrical contact with the resistor strip at an angular location at which the conductor strip is engaged by the wiper.

24. The medication delivery device of any one of aspects 10-23, wherein the second member comprises a core member having an interior surface defining a bore in which the first member rotates, the sensing band layering the interior surface.

25. The medication delivery device of aspect 24, wherein the core member includes an exterior surface and an opening extending between the interior surface and the exterior surface, the sensing band including a connector leg having electrical leads passing through the opening and wrapping along the exterior surface.

26. The medication delivery device of aspect 24, wherein the sensing band is a first sensing band and the wiper is a first wiper, and further including a third member of the medication delivery device rotatable relative to the core member about the axis of rotation in proportion to at least one of an amount of a dose set and an amount of a dose delivered by operation of the medication delivery device, the sensing system further including a second wiper rotationally coupled to the third member and projecting inward or outward in the radial direction, and a second sensing band rotationally coupled to the core member, the second sensing band wrapping along a surface of the core member for operational contact with the second wiper as the third member rotates relative to the core member, the second sensing band having an electrical characteristic correlated with where the second sensing band is operationally engaged by the second wiper.

27. The medication delivery device of aspect 26, wherein the first and second sensing bands directly sandwich the core member therebetween.

28. The medication delivery device of aspect 26, wherein the second sensing band is positioned at a location in the radial direction between the first sensing band and the second wiper.

29. The medication delivery device of aspect 24, wherein the core member is separately formed and rotatably fixed to a housing of the medication delivery device.

30. A medication delivery device for delivering medication from a cartridge having a barrel holding the medication between a movable plunger and an outlet, the medication delivery device including: a main housing; a cartridge housing for holding the cartridge extending from the main housing; a drive member including a forward end for engaging the movable plunger, the drive member having a length extending in an axial direction within the main housing; a dose delivery mechanism for controlling advancement of the drive member forward within the main housing in the axial direction to move the movable plunger for delivering medication through the outlet, the dose delivery mechanism including a first member rotatable relative to the main housing in proportion to one of an amount of a dose set and an amount of a dose delivered by operation of the medication delivery device, the first member relatively rotatable to the main housing about an axis of rotation extending in the axial direction; a sensing system operable to detect relative rotational positions of the first member and the main housing and generate outputs correlated to such relative rotational positions, the sensing system including; a first wiper coupled to the first member and projecting in a radial direction; a first sensing band coupled to the main housing, the first sensing band arranged in a curved shape around the axis of rotation and having a first operational angular length, the first sensing band disposed in the radial direction inward or outward of the first wiper for a physical contact with the first wiper during rotation of the first member relative to the main housing, the first sensing band having an electrical characteristic correlated with where along the first operational angular length the first sensing band is operationally engaged in the radial direction due to the physical contact with the first wiper; and a controller in electrical communication with the sensing system to identify, based on outputs of the sensing system, at least one of the amount of the dose set and the amount of the dose delivered by operation of the medication delivery device.

31. The medication delivery device of aspect 30, wherein the first sensing band is rotationally coupled to the main housing via a core member, the core member being separately formed and rotatably fixed to the main housing.

32. The medication delivery device of aspect 31, wherein the first sensing band is disposed on the core member and the core member is axially movable within the main housing, the first wiper fixedly coupled to the first member to move axially therewith, the first member axially movable within the main housing during operation of the medication delivery device, and wherein the core member and the first sensing band are constrained to move axially with the first member to maintain alignment of the first wiper with the first sensing band.

33. The medication delivery device of aspect 30, wherein the first sensing band is rotationally coupled to the main housing via a core member having an interior surface defining a bore in which the first member is rotationally disposed, the first sensing band wrapping along the interior surface and disposed in the radial direction outward of the first wiper.

34. The medication delivery device of aspect 33, further including a second member of the medication delivery device rotatable relative to the core member about the axis of rotation in proportion to the other of the amount of a dose set and the amount of a dose delivered by operation of the medication delivery device, the sensing system further including a second wiper rotationally coupled to the second member and projecting inward in the radial direction, and a second sensing band rotationally coupled to the main housing via the core member and circuited with the electrical power source, the second sensing band arranged in a curved shape around the axis of rotation and having a second operational angular length, the second sensing band wrapping along an exterior surface of the core member and disposed in the radial direction inward of the second wiper for a physical contact with the second wiper as the second member rotates relative to the main housing, the second sensing band including a third electrical strip and a fourth electrical strip being in electrical contact along the second operational angular length where the second sensing band is operationally engaged in the radial direction due to physical contact with the second wiper, the third electrical strip and the fourth electrical strip being spaced in the radial direction and out of electrical contact along the second operational angular length where the second sensing band is not operationally engaged in the radial direction due to physical contact with the second wiper, the second sensing band having an electrical characteristic correlated with where along the second operational angular length the second sensing band is operationally engaged in the radial direction due to the physical contact with the second wiper.

35. The medication delivery device of aspect 34, wherein the first sensing band includes a first electrical strip and a second electrical strip being in electrical contact along the first operational angular length where the first sensing band is operationally engaged in the radial direction due to physical contact with the first wiper, the first electrical strip and the second electrical strip being spaced in the radial direction and out of electrical contact along the first operational angular length where the first sensing band is not operationally engaged in the radial direction due to physical contact with the first wiper, wherein the first and second sensing bands directly sandwich the core member therebetween.

36. The medication delivery device of aspect 35, wherein the first and second electrical strips include a main portion and a secondary portion, the secondary portion jutting directly from the main portion in the axial direction, the first wiper being in an axial position to engage the main portion but not the secondary portion, and wherein the sensing system comprises a second wiper in an axial position to engage the secondary portion but not the main portion.

37. The medication delivery device of any one of aspects 34-36, wherein the first wiper and the second wiper are angularly spaced about the axis of rotation.

38. The medication delivery device of any one of aspects 34-37, where the second wiper extends axially further than the first wiper.

39. The medication delivery device of any one of aspects 34-38, where the second wiper is circumferentially disposed relative to the first wiper by substantially 180 degrees.

40. The medication delivery device of any one of aspects 30-39, further including a pair of first wipers coupled to the first member, and a pair of first sensing bands coupled to the main housing in physical contact with the respective first wipers.

We claim:

1. A medication delivery device comprising:
   a first member and a second member rotatable relative to the first member about an axis of rotation in proportion to an amount of a dose set by operation of the medication delivery device;
   a third member and a fourth member rotatable relative to the third member about the axis of rotation in proportion to an amount of a dose delivered by operation of the medication delivery device;
   a first wiper coupled to said first member and projecting in a first radial direction;
   a second wiper coupled to said third member and projecting in a second radial direction;
   an electrically operable first sensing band coupled to said second member;
   an electrically operable second sensing band coupled to said fourth member, each of the first and second sensing bands arranged in a curved shape and radially disposed relative to and in a contacting relationship with the first and second wipers, respectively, wherein, during relative rotation between said first and second members and relative rotation between said third and fourth members, each of said first and second sensing bands is operable to generate outputs associated with relative angular positions of the corresponding first and second wipers along an operational angular length of the respective first and second sensing bands that is indicative of relative rotational positions of said first and second members and said third and fourth members; and
   a controller electrically coupled with each of said first and second sensing bands to determine, based on the outputs generated by said first and second sensing bands, the amount of the dose set and the amount of the dose delivered by operation of the medication delivery device.

2. The medication delivery device of claim 1, wherein the second member and the fourth member are integrally formed as a single core member.

3. The medication delivery device of claim 1, further comprising a pair of first wipers coupled to said first member and a pair of second wipers coupled to the third member.

4. The medication delivery device of claim 3, further comprising a pair of electrically operable first sensing bands coupled to said second member and associated with the pair of first wipers; and a pair of electrically operable second sensing bands coupled to said fourth member and associated with the pair of second wipers.

5. The medication delivery device of claim 1, further comprising a medication.

6. A medication delivery device comprising:
   a first member of the medication delivery device;
   a second member of the medication delivery device rotatable relative to the first member in proportion to at least one of an amount of a dose set and an amount of a dose delivered by operation of the medication delivery device, said first and second members relatively rotatable about an axis of rotation extending in an axial direction;
   a sensing system operable to detect relative rotational positions of said first and second members and generate outputs correlated to such relative rotational positions, said sensing system comprising:
   a wiper rotationally coupled to said first member and projecting in a radial direction;
   a sensing band rotationally coupled to said second member and circuited with an electrical power source, said sensing band arranged in a curved shape around the axis of rotation and having an operational angular length, said sensing band disposed radially inward or outward of said wiper for a physical contact with said wiper as said second member rotates relative to said first member, said sensing band having an electrical characteristic correlated with where along said operational angular length of said sensing band is operationally engaged due to the physical contact with said wiper; and
   a controller electrically circuited with said sensing system to identify, based on outputs of said sensing system, at least one of the amount of the dose set and the amount of the dose delivered by operation of the medication delivery device.

7. The medication delivery device of claim 6, wherein at least one of said wiper and said sensing band is radially resilient to assist maintenance of said wiper and said sensing band in physical contact as said second member rotates relative to said first member.

8. The medication delivery device of claim 6, wherein said sensing band is disposed radially outward of said wiper.

9. The medication delivery device of claim 8, wherein said second member comprises a housing of the medication delivery device.

10. The medication delivery device of claim 9, wherein said sensing band is attached directly to an interior circumferential surface of said housing.

11. The medication delivery device of claim 9, wherein said sensing band is disposed on a component that is at least rotatably fixedly mounted to said housing.

12. The medication delivery device of claim 6, wherein said operational angular length extends only partially around a circumference of said second member.

13. The medication delivery device of claim 12, wherein said operational angular length extends at least 345 degrees but less than 360 degrees around an inner circumference of said second member.

14. The medication delivery device of claim 6, wherein said sensing system comprises a second wiper rotationally coupled to said first member and projecting in a second radial direction, and a second sensing band rotationally coupled to said second member and said electrical power source, said second sensing band arranged in a curved shape around the axis of rotation and having an operational angular length, said second sensing band disposed radially inward or outward of said second wiper for a physical contact with said second wiper as said second member rotates relative to said first member, said second sensing band having an electrical characteristic correlated with where along said operational angular length of said second sensing band is engaged due to the physical contact with said second wiper.

15. The medication delivery device of claim 14, wherein said operational angular lengths of said sensing band and said second sensing band are axially spaced and each only partially extends around a circumference of said second member.

16. The medication delivery device of claim 15, wherein said wiper and said second wiper comprise different regions of a single wiper body.

17. The medication delivery device of claim 6, wherein said sensing system and said controller are parts of a reusable dose delivery detection module, said reusable dose delivery detection module removable from said first member and said second member for subsequent mounting to corresponding members of another medication delivery device for use therewith.

18. The medication delivery device of claim 6, wherein said sensing band is disposed radially outward of said wiper, said sensing band comprising a resistor strip and a conductor strip, said conductor strip disposed radially inward of said resistor strip and bendable radially outward into electrical contact with said resistor strip at an angular location at which said conductor strip is engaged by said wiper.

19. The medication delivery device of claim 6, wherein said second member comprises a core member having an interior surface defining a bore in which said first member rotates, said sensing band layering said interior surface.

20. The medication delivery device of claim 19, wherein said core member includes an exterior surface and an opening extending between said interior surface and said exterior surface, said sensing band including a connector leg having electrical leads passing through said opening and wrapping along said exterior surface.

21. The medication delivery device of claim 19, wherein said sensing band is a first sensing band and said wiper is a first wiper, and wherein said second member is rotatable relative to said first member in proportion to the amount of the dose set, and wherein the medication delivery device further comprises a third member of the medication delivery device rotatable relative to the core member about the axis of rotation in proportion to the amount of the dose delivered by operation of the medication delivery device, said sensing system further comprising a second wiper rotationally coupled to said third member and projecting radially inward or outward, and a second sensing band rotationally coupled to said core member, said second sensing band wrapping along a surface of said core member for operational contact with said second wiper as said third member rotates relative to said core member, said second sensing band having an electrical characteristic correlated with where said second sensing band is operationally engaged by said second wiper.

22. The medication delivery device of claim 6, further comprising a medication.

* * * * *